United States Patent
Delagrave et al.

(10) Patent No.: US 6,635,453 B2
(45) Date of Patent: Oct. 21, 2003

(54) METHODS FOR THE ENZYMATIC ASSEMBLY OF POLYNUCLEOTIDES AND IDENTIFICATION OF POLYNUCLEOTIDES HAVING DESIRED CHARACTERISTICS

(75) Inventors: Simon Delagrave, Avondale, PA (US); Barry Marrs, Kennett Square, PA (US)

(73) Assignee: Hercules Incorporated, Wilmington, DE (US)

( * ) Notice: Subject to any disclaimer, the term of this patent is extended or adjusted under 35 U.S.C. 154(b) by 9 days.

(21) Appl. No.: 09/852,385

(22) Filed: May 10, 2001

(65) Prior Publication Data

US 2003/0082536 A1 May 1, 2003

Related U.S. Application Data

(63) Continuation-in-part of application No. 09/571,774, filed on May 16, 2000, now Pat. No. 6,479,262.

(51) Int. Cl.[7] .............................. C12P 19/34; C12Q 1/68
(52) U.S. Cl. ......................................... 435/91.1; 435/6
(58) Field of Search .................................... 435/6, 91.1

(56) References Cited

U.S. PATENT DOCUMENTS

| | | | |
|---|---|---|---|
| 4,458,066 A | 7/1984 | Caruthers et al. | 536/27 |
| 5,602,000 A | 2/1997 | Hyman | 435/91.1 |
| 5,723,323 A | 3/1998 | Kauffman et al. | 435/172.3 |
| 5,763,192 A | 6/1998 | Kauffman et al. | 435/7.1 |
| 5,814,476 A | 9/1998 | Kauffman et al. | 435/69.1 |
| 5,817,483 A | 10/1998 | Kauffman et al. | 435/69.1 |
| 5,914,245 A | 6/1999 | Bylina et al. | 435/19 |
| 5,935,527 A | 8/1999 | Andrus et al. | 422/131 |
| 5,942,609 A | 8/1999 | Hunkapiller et al. | 536/25.3 |
| 6,117,679 A | 9/2000 | Stemmer | 435/440 |
| 6,159,690 A | * 12/2000 | Borrebaeck et al. | 435/6 |
| 6,171,820 B1 | 1/2001 | Short | 435/69.1 |

FOREIGN PATENT DOCUMENTS

| | | |
|---|---|---|
| DE | 43 43 591 A1 | 6/1995 |
| DE | 196 33 427 A1 | 3/1998 |
| DE | 198 12 103 A1 | 9/1999 |
| DE | 199 28 591 A1 | 12/1999 |
| EP | 0 406 937 | 1/1991 |
| EP | 1 149 905 A1 | 10/2001 |
| GB | 2 169 605 A | 7/1986 |
| WO | WO 83/02626 | 8/1983 |
| WO | WO 90/00626 | 1/1990 |
| WO | WO 93/19202 | 9/1993 |
| WO | WO 94/14972 | 7/1994 |
| WO | WO 98/27230 | 6/1998 |
| WO | WO 99/14318 | 3/1999 |
| WO | 00/58517 A1 | 10/2000 |
| WO | 00/77261 A1 | 12/2000 |

OTHER PUBLICATIONS

English translation of the German Patent No. DE 19812103 A1 to Bernauer.*

Nord, K. et al., "A combinatorial library of an alpha–helical bacterial receptor domain," *Protein Engineering*, 1995, 8(6), 601–608.

(List continued on next page.)

*Primary Examiner*—Kenneth R. Horlick
*Assistant Examiner*—Teresa Strzelecka
(74) *Attorney, Agent, or Firm*—Woodcock Washburn LLP

(57) ABSTRACT

The present invention provides methods of preparing large polynucleotides of arbitrary sequence and in a manner that will readily lend itself to automation. The present invention provides methods of preparing a polynucleotide having at least 200 nucleotides in either a 5' to 3' or 3' to 5' direction by ligating a plurality of oligonucleotides, the assembly of which, represents the nucleotide sequence of the desired polynucleotide. The present invention also provides libraries of polynucleotides and screening of libraries for polynucleotide members having desired properties.

26 Claims, 4 Drawing Sheets

OTHER PUBLICATIONS

Rayner, S. et al., "MerMade: An oligodeoxyribonucleotide synthesizer for high throughput oligonucleotide production in dual 96–well plates," *PCR Methods and Applications*, Jul. 1998, 8(7), Cold Spring Harbor, NY, 741–747.

Kikuchi, M. et al., "An effective family shuffling method using single–stranded DNA", *Gene*, 2000, 243, 133–137.

Vratskikh, LV. et al., "Solid–phase synthesis of oligoribonucleotides using T4 RNA ligase and T4 polynucleotide kinase", *Biochimie*, 1995, 77(4), 227–232.

Arkin, A. et al., "An algorithm for protein engineering: Simulations of recursive ensemble mutagenesis", *Proc. Natl. Acad. Sci. USA*, Aug. 1992, 89, 7811–7815.

Beattie, K. et al., "Solid–phase gene assembly", *Nature*, Aug. 8, 1991, 352, 548–549 and 742.

Chapman, D. et al., "Nucleotide and deduced amino acid sequence of stp: The bacteriophage T4 anticodon nuclease gene", *J. Mol. Biol.*, 1988, 199, 373–377.

Chen, H., et al., "A new method for the synthesis of a structural gene", *Nucleic Acids Research*, Jan. 25, 1990, 18(4), 871–878.

Chen, K., et al., "Tuning the activity of an enzyme for unusual environments: sequential random mutagenesis of subtilisin E for catalysis in dimethylformamide," *Proc. Natl. Acad. Sci. USA*, 1993, 90, 5618–5622.

Chen, K., et al., "Enzyme engineering for nonaqueous solvents: random mutagenesis to enhance activity of subtilisin E in polar organic media," *Biotechnology*, 1991, 9, 1073–1077.

Chu, B.C.F., et al., "Ligation of oligonucleotides to nucleic acids or proteins via disulfide bonds," *Nuc. Acids Res.*, 1988, 16(9), 3671–3691.

Coco, et al., "DNA shuffling method for generating highly recombined genes and evolved enzymes", *Nature Biotechnology*, 2001, 19, 354.

Delagrave, S., et al., "Recursive ensemble mutagenesis," *Protein Eng.*, 1993, 6, 327–331.

Dove, A., "Opinions evolve on Kauffman patent", *Nature Biotechnology*, Apr. 2000, 18, 373.

Harada, K., et al., "In vitro selection of optimal DNA substrates for T4 RNA ligase," *Proc. Natl. Acad. Sci., USA*, 1993, 90, 1576–1579.

Heaphy, S. et al., "Effect of single amino acid changes in the region of the adenylation site of T4 RNA ligase", *Biotechnology*, 1987, 26(6), 1688–1696.

Ho, S. et al., "Site–directed mutagenesis by overlap extension using the polymerase chain reaction", *Gene*, 1989, 77, 51–59.

Horn, T., et al., "A chemical 5'–phosphorylatin of oligodeoxyribonucleotides that can be monitored by trityl cation release," *Tetra. Lett.*, 1986, 27, 4705–4708.

Horton R. et al., "Engineering hybrid genes without the use of restriction enzymes: gene splicing by overlap extension", *Gene*, 1989, 77, 61–68.

Hostomský, Z. et al., "Solid–phase assembly of cow colostrum trypsin inhibitor gene", *Nucleic Acids Research*, 1987, 15, 4849–4856.

Hostomský, Z. et al., "Solid–phase assembly of DNA duplexes from synthetic oligonucleotides", *Nucleic Acids Research*, 1987, Symposium Series No. 18, 241–244.

Howitt C., "Improved ligation–anchored PCR strategy for identification of 5' ends of transcripts", *BioTechniques*, Jul. 1996, 21, 34–38.

Isono, Y., et al., "Purification and reaction of a new enzyme, nucleoside oxidase," *Agric. Biol. Chem.*, 1989, 53, 1663–1669.

Ivanov, I. et al., "Two methods for rapid assembly and oligomerization of synthetic genes: construction of human calcitonin–encoding sequences", *Gene*, 1990, 95, 295–299.

Joo, H., et al., "A high–throughput digital imaging screen for the discovery and directed evolution of oxygenases," *Chem. Biol.*, 1999, 6(10), 699–706.

Joo, H., et al., "Laboratory evolution of peroxide–mediated cytochrome P450 hydroxylation," *Nature*, 1999, 399, 670–673.

Kinoshita, Y. et al., "Unexpectedly general replaceability of ATP in ATP–requiring enzymes", *J. Biochem.*, 1997, 122, 205–211.

Kinoshita, Y., et al., "Fluorescence–, isotope–or biotin–labeling of the 5'–end of single–stranded DNA/RNA using T4 RNA ligase", *Nucleic Acids Research*, 1997, 25, 3747–3748.

Krug, M. et al., "Reversal of T4 RNA ligase", *Biochemistry*, 1982, 21(8), 1858–1864.

Leung, D.W., et al., "A method for random mutagenesis of a defined DNA segment using a modified polymerase chain reaction," *J. Methods in Cell and Molec. Biol.*, 1989, 1, 11–15.

Marrs, B., et al., "Novel approaches for discovering industrial enzymes," *Curr. Opin. Microbiol.*, 1999, 2, 241–245.

McLaughlin, L. et al., "Donor activation in the T4 RNA ligase reaction", *Biochemistry*, 1985, 24, 267–273.

Miyazaki, K., et al., "Exploring nonnatural evolutionary pathways by saturation mutagenesis: rapid improvement of protein function," *J. Mol. Evol.*, 1999, 49, 716–720.

Mudrakovskaia, A.V., et al., "Solid–phase enzymatic synthesis of oligoribonucleotides," Plenum Publ. Corp., 1992, translatd from *Bioorganicheskaya Khimiya*, 17(6), 1991, 819–822; Plenum Publishing Corp., 1992, 469–472.

Mullinax, R. et al., "Expression of a heterodimeric Fab antibody protein in one cloning step", *BioTechniques*, 1992, 12, 864–869.

Nijhuis, M. et al., "Enzymatically produced composite primers, An application of T4 RNA ligase–coupled primers to PCR", *BioTechniques*, 1995, 19, 182–186.

Nishigaki, K. et al., "Y–ligation: An efficient method for ligating single–stranded DNAs and RNAs with T4 RNA ligase", *Molecular Diversity*, 1998, 4, 187–190.

Pantoliano, M. et al., "Large increases in general stability for subtilisin BPN' through incremental changes in the free energy of unfolding," *Biochemistry*, 1989, 28, 7205–7213.

Pierce, J., "In–frame cloning of large synthetic genes using moderate–size oligonucleotides", *BioTechniques*, 1994, 16(4), 708–714.

Profy, A. et al., "Synthesis of 2' (3')–O–DL–alanyl hexainosinic acid using T4 RNA ligase: suppression of the enzymic reverse transfer reaction by alkaline phosphatase", *Nucleic Acids Research*, 1983, 11(5), 1617–1633.

Rand, K. et al., "Sequence and cloning of bacteriophage T4 gene 63 encoding RNA ligase and tail fibre attachment activities", *The EMBO Journal*, 1984, 3(2), 397–402.

Sambrook, et al. (eds.), *Molecular Cloning: A Laboratory Manual*, Cold Spring Harbor Laboratory Press, Cold Spring Harbor, NY, 1989.

Sambrook, et al., *Molecular Cloning a Laboratory Manual*, $2^{nd}$ Ed., cold Spring Harbor Press, 1989.

Schmitz C. et al., "Solid–phase enzymatic synthesis of oligonucleotides", *Org. Lett.*, 1999, 1(11), 1729–1731.

Sillero, A. et al., "Synthesis of dinucleoside polyphosphates catalyzed by firefly luciferase and several ligases", *Pharmacology & Therapeutics*, 2000, 87, 91–102.

Sninsky, J. et al., "The use of terminal blocking groups for the specific joining of oligonucleotides in RNA ligase reactions containing equimolar concentrations of acceptor and donor molecules", *Nucleic Acids Research*, 1976, 3(11), 3157–3166.

Stahl, S. et al., "Solid–phase gene assembly of contructs derived from the *Plasmodium falciparum* malaria blood–stage antigen Ag332", *BioTechniques*, 1993, 11(3), 425–434.

Stemmer, W. et al., "Single–step assembly of a gene and entire plasmid from large numbers of oligodeoxyribonucleotides", *Gene*, Oct. 16, 1995, 164(1), 49–53.

Stemmer, W., "DNA shuffling by random fragmentation and reassembly: In vitro recombination for molecular evolution", *Proc. Natl. Acad. Sci. USA*, Oct. 1994, 91, 10747–10751.

Sugino et al., "Bacteriophage T4 RNA ligase: Reaction intermediates and interaction of substrates", *J Biol Chem*, Mar. 10, 1977, 252(5):1732–8.

Tessier, D.C., et al., "Ligation of single–stranded oligodeoxyribonucleotides by T4 RNA ligase," *Analytical Bioc.*, 1986, 158, 171–178.

Uemura, A., et al., "Lipase–catalyzed regioselective acylation of sugar moieties of nucleosides," *Tetra. Letts.*, 1989, 30(29), 3817–3818.

Uhlenbeck, O. et al., "Equimolar addition of oligoribonucleotides with T4 RNA ligase", *Nuceic Acids Research*, 1977, 4(1), 85–98.

Wong, C., et al., "Enzymes in organic synthesis: use of subtilisin and a highly stable mutant derived from multiple site–specific mutations," *J. Am. Chem. Soc.*, 1990, 112, 945–953.

Ye, Q. et al., "Gene synthesis and expression in *E. coli* for Pump, a human matrix metalloproteinase", *Biochem. Biophys. Res. Commun.*, Jul. 15, 1992, 186(1), 13–149.

You, L., et al., "Directed evolution of subtilisin E in *Bacillus subtilis* to enhance total activity in aqueous dimethylformamide," *Protein Eng.*, 1994, 9(1), 77–83.

Yu, Y. et al., "A new strategy for introducing photoactivatable 4–thiouridine ($^{4S}$U) into specific positions in a long RNA molecule", *RNA*, 1997, 3, 807–810.

Zhang, X., et al., "Single–stranded DNA ligation by T4 RNA ligase for PCR cloning of 5'–noncoding fragments and coding sequence of a specific gene," *Nuc. Acids Res.*, 1996, 24(5), 990–991.

\* cited by examiner

METHODS FOR THE ENZYMATIC ASSEMBLY OF POLYNUCLEOTIDES AND IDENTIFICATION OF POLYNUCLEOTIDES HAVING DESIRED CHARACTERISTICS

CROSS REFERENCE TO RELATED APPLICATIONS

This is a continuation-in-part of application Ser. No. 09/571,774, filed May 16, 2000 now U.S. Pat. No. 6,479,262.

FIELD OF THE INVENTION

The present invention relates generally to processes for the synthesis of polynucleotides, such as DNA and fragments of DNA, RNA and fragments of RNA, plasmids, genes, and chemically and/or structurally modified polynucleotides. The present invention also relates to the generation of libraries of polynucleotides, library screening and identification of library members having desired characteristics.

BACKGROUND OF THE INVENTION

Living cells can be "reprogrammed," in vitro or in vivo, to produce useful amounts of desired proteins or other compounds by introducing the appropriate nucleic acids (DNA or RNA) into them; this concept is the keystone of modem biotechnology. The construction of recombinant DNA molecules necessary to achieve this "reprogramming" or to perform a varied and growing number of other functions is a frequent and necessary activity of molecular biology research and of biotechnological endeavors in industrial and academic settings. By improving the process by which DNA or RNA molecules of arbitrary sequence are made, a significant increase of productivity in biotechnology could be achieved, resulting in benefits in many fields including medical research, agriculture and the chemical industry. For example, numerous efforts to sequence the entire genomes of a variety of organisms (microbes, animals and plants) have generated many large databases of gene sequences. These genes can be made and studied experimentally through laborious and time-consuming techniques involving the isolation and subsequent manipulation (generally referred to as molecular cloning) of DNA from the organism in which the gene is found and/or expressed. Alternatively, inefficient DNA synthesis methods can be used, as described below.

The ability to synthesize large RNA or DNA molecules (e.g., entire genes) is of value to any endeavor that relies on recombinant DNA technology. As alluded to above, DNA molecules of arbitrary sequence can be synthesized in vitro. A solid phase method to synthesize oligonucleotides that is now widely used in commercial DNA synthesizers is reported in U.S. Pat. No. 4,458,066. Current DNA synthesizers, however, are limited to the production of relatively short single-stranded DNA oligonucleotide molecules of length typically less than 200 nucleotides (nt). In contrast, the average prokaryotic gene is 1000 basepairs (bp) in length, a eukaryotic cDNA is frequently longer than 2000 bp, and most plasmids are larger than 3000 bp. Although state-of-the-art oligonucleotide synthesizers relying on beta-cyanoethyl phosphoramidite chemistry (U.S. Pat. No. 5,935,527) can make and purify 48 oligonucleotides in less than 48 hours (25 nt/oligox48 oligonucleotides=1200 nt, a typical bacterial gene), it is still very time consuming and labor-intensive to assemble these oligonucleotides together into a single gene.

Gene synthesis, a service frequently offered commercially by oligonucleotide manufacturers, is expensive (approximately $10 to $20/bp) and slow (frequently requiring several weeks) because current methods are labor-intensive. A method to make relatively large DNA molecules by mixing two long oligonucleotides (up to 400 nt) and amplifying the desired double-stranded DNA fragment from the mixture using the polymerase chain reaction (PCR) is reported in European Patent Application 90201671.6. This method becomes more complicated and requires extensive manipulations by a skilled technician when molecules larger than 400 bp must be synthesized. Similar statements can be made of the method of Khorana, *Science*, 1979, 203, 614–625.

A method to synthesize long nucleic acid molecules in which a ribo- or deoxyribo-oligonucleotide attached to a solid support is extended by the sequential addition of other "assembly" oligonucleotides is reported in U.S. Pat. No. 5,942,609 and Chen, et al., *Nucleic Acids Res.*, 1990, 18, 871. Of key importance to this process is the annealing of a partially complementary "bridging" oligonucleotide to the two oligonucleotides that will be covalently linked together by a ligase. Although this method will likely achieve its stated goal of synthesizing long polynucleotides, the need for the synthesis of a bridging oligonucleotide adds to the total number of oligonucleotides which must be synthesized and purified, with an attendant increase in costs and time of synthesis. In addition, the assembly of a complex mixture of oligonucleotides would greatly complicate this process because of the large number of different bridging oligonucleotides that would be needed to bring together the assembly oligonucleotides. Moreover, it would be advantageous to obviate the need for the annealing step required to productively bind the bridging oligonucleotide to its target assembly oligonucleotides. Such a step may introduce complications due to the need to avoid non-specific hybridization problems. Complications may include the need to carefully control hybridization temperatures over lengthy incubation periods as well as to carefully design each bridging oligonucleotides to bind specifically to the desired sequence.

International Publication WO 83/02626 reports a method of assembling a polyribonucleotide using the enzyme T4 RNA ligase, including time-consuming purification steps, but does not include the use of solid phase methods which would facilitate automation and increase the reliability of the process. In contrast, Mudrakovskaia et al. (*Bioorg. Khim.*, 1991, 17, 819–822) report a "solid-phase enzymic synthesis of oligoribonucleotides" but do not disclose how the method could be used to couple more than a few nucleotides to a tethered oligonucleotide. Similarly, Schmitz, et al., (*Org. Lett.*, 1999, 1, 1729) describes the synthesis of short oligonucleotides from mononucleotide building blocks using T4 RNA ligase, but reports exceedingly long reaction times, militating against the formation of longer sequences. Neither International Publication WO 83/02626, Mudrakovskaia et al., nor Schmitz, et al. disclose how their methods could be used to synthesize large (>200 nt) DNA or RNA molecules without requiring numerous and laborious purification steps.

Harada et al. (*Proc. Natl. Acad. Sci. USA*, 1993, 90, 1576–1579) reports in vitro selection techniques to characterize DNA sequences that are ligated efficiently by T4 RNA ligase. Tessier et al. (*Anal. Biochem.*, 1986, 158, 171–178) reports a set of reaction conditions for ligation of DNA fragments up to 40 bases in length. Zhang et al. (*Nuc. Acids Res.*, 1996, 24, 990–991) reports single-stranded DNA ligation by T4 RNA ligase for PCR cloning of 5' noncoding fragments and coding sequence of a particular gene. Ligation of oligonucleotides using T4 RNA ligase has also been reported in Walker, et al., *Proc. Natl. Acad. Sci. USA,* 1975, 72, 122 and Ohtsuka, et al, *Nucleic Acids Res.,* 1976, 3, 1613, but the technique was recognized as problematic due to the accumulation of unwanted by-products (Krug, et al., *Biochemistry,* 1982, 21, 1858).

The enhanced ability for de novo synthesis of large polynucleotides or genes may greatly facilitate the preparation of combinatorial libraries of polynucleotides because it would be much more efficient than existing methods. For example, combinatorial libraries of genes can be made by cassette mutagenesis (Oliphant, et al., *Gene,* 1986, 44, 177 and Oliphant, et al., *Proc. Natl. Acad. Sci. USA,* 1989, 86, 9094) whereby genes with random combinations of nucleotides are created. Similarly, U.S. Pat. Nos. 5,723,323; 5,763,192; 5,814,476; and 5,817,483 describe libraries of expression vectors having stochastic DNA regions. By simultaneously randomly mutating fifteen nucleotides of a gene, a billion different sequences can be generated. Current methods of screening and molecular cloning often limit the number of sequences that can be screened to a much smaller number. Although there are examples of libraries with $10^8$ individual mutants (Cwirla, et al., *Proc. Natl. Acad. Sci USA,* 1990, 87, 6378), certain screening methods to identify useful enzymes are limited to a few thousand mutants. A process to optimize combinatorial libraries has been proposed (Arkin, et al., *Proc. Natl. Acad. Sci. USA,* 1992, 89, 7811) and tested (Delagrave, et al., *Protein Eng.,* 1993, 6, 327 and Delagrave, et al., *Biotechnology,* 1993, 11, 1548) to circumvent this problem. A related approach has also been proposed to deal with the combinatorial diversity of phylogenies of protein sequences (Goldman, et al., *Biotechnology,* 1992, 10, 1557). However, these methods consider only libraries having degeneracies at the nucleotide level. In some instances, such as for large sets of phylogenically related sequences, combinatorial libraries where degeneracies are at the oligonucleotide level (i.e., blocks of nucleotides), rather than at the nucleotide level, are more favorable. This difference would allow alteration of an entire sequence instead of just a few nucleotides.

In an effort to prepare populations of polynucleotides, a method referred to as DNA shuffling has been developed. According to this method, described in U.S. Pat. No. 6,117, 679 and Stemmer, et al., *Proc. Natl. Acad. Sci. USA,* 1994, 91, 10747, a series of related polynucleotides are isolated, fragmented, and recombined to form a population of polynucleotide variants. The recombination of related polynucleotides proceeds via hybridization of complementary or partially complementary fragments. The requirement for hybridization limits this method to polynucleotides with a certain minimal amount of homology. Moreover, recombination between polynucleotides tends to occur at points of high sequence identity which are found randomly along the sequences. There is, therefore, little control of the sites of recombination during a shuffling experiment. Furthermore, DNA shuffling methods are not amenable to working with RNA. However, in certain cases it may be advantageous to work directly with RNA molecules. For example, many viral genomes consist of single strands of RNA like flaviviruses such as Dengue, Japanese Encephalitis and West Nile, retroviruses such as HIV, and other animal and plant pathogens, including viroids (*Fundamental Virology,* Lippincott-Raven, Philadelphia, Pa., 1996) By constructing recombinant viral genomes, valuable vaccines may be developed (Guirakhoo, et al., *Virology,* 1999, 257, 363 and Monath, et al., *Vaccine,* 1999, 17, 1868), and the availability of methods to synthesize and recombine RNA more rapidly may accelerate this type of research.

A method of synthesizing large polynucleotides (such as RNA or DNA molecules longer than 200 bp) of arbitrary or predefined sequence and in a manner that will more readily lend itself to automation is desired. In addition, an improved version of the enzyme T4 RNA ligase that would increase the ability of this enzyme to catalyze the ligation of two oligonucleotides is also desired. Ideally, the improved enzyme would catalyze efficiently the ligation of oligonucleotides. Also, the ability of the enzyme to carry out these reactions at an elevated temperature or to use ddATP instead of ATP would be valuable properties in an improved ligase. By increasing the productivity of gene synthesis in laboratories, the present invention would improve scientists' ability to find, for example, enzymes capable of catalyzing reactions necessary to synthesize a new drug.

All in all, de novo gene synthesis is a powerful technique that when fully optimized would contribute greatly to the fields of biotechnology and medicine. Not only would gene synthesis facilitate the manipulation of large polynucleotides by offering, for example, better control over the positioning of restriction sites or optimization of regions of sequence governing gene expression; the ability to synthetically build a gene would allow the directed and rapid formation of combinatorial gene libraries. Screening of these libraries for genes with desired properties may allow the discovery or development of new and improved biomolecules such as enzymes with increased activity or receptors with higher ligand affinity. Thus, new methods for the synthesis of polynucleotides are needed, and the present invention is directed toward this need, as well as others.

SUMMARY OF THE INVENTION

The present invention provides methods of preparing large polynucleotides (such as RNA or DNA molecules longer than 200 bp) of arbitrary sequence and in a manner that will more readily lend itself to automation than existing methods.

One aspect of the present invention is directed to methods of preparing a polynucleotide having at least 200 nucleotides and a predetermined nucleotide sequence comprising: providing a solid support, providing a plurality of oligonucleotides, wherein the combination of the nucleotide sequences of the oligonucleotides comprises the nucleotide sequence of the polynucleotide, contacting the solid support with the 3' terminus of a first oligonucleotide from the plurality of oligonucleotides to form a tethered oligonucleotide, ligating the 3' terminus of another oligonucleotide from the plurality of oligonucleotides to the 5' terminus of the tethered oligonucleotide, and repeating the ligation with other oligonucleotides until the polynucleotide is prepared.

Another aspect of the present invention is directed to methods of preparing a polynucleotide having at least 200 nucleotides and a predetermined nucleotide sequence comprising: providing a solid support, providing a plurality of oligonucleotides, wherein the combination of the nucleotide sequences of the oligonucleotides comprises the nucleotide sequence of the polynucleotide, contacting the solid support with the 5' terminus of a first oligonucleotide from the plurality of oligonucleotides to form a tethered oligonucleotide, ligating the 5' terminus of another oligonucleotide from the plurality of oligonucleotides to the 3' terminus of the tethered oligonucleotide, and repeating the ligation with other oligonucleotides until the polynucleotide is prepared.

The present invention further embodies, inter alia, a method of preparing a polynucleotide from a plurality of oligonucleotides, the method comprising blocking the 3' terminus of a first oligonucleotide with a blocking group to form a blocked oligonucleotide, wherein the first oligonucleotide comprises the 3' terminus of the polynucleotide; coupling the 3' terminus of a further oligonucleotide from the plurality of oligonucleotides to the 5' terminus of the blocked oligonucleotide to form a coupled oligonucleotide; amplifying the coupled oligonucleotide to form an amplified oligonucleotide substantially free of blocking group; and repeating the blocking, coupling, and amplifying steps with the amplified oligonucleotide until the polynucleotide is prepared.

The present invention further embodies a method of preparing a polynucleotide from a plurality of oligonucleotides, the method comprising blocking the 3' terminus of each of the oligonucleotides, except for an unblocked oligonucleotide comprising the 5' terminus of the polynucleotide, with a blocking group to form a plurality of blocked oligonucleotides; coupling the 3' terminus of the unblocked oligonucleotide with the 5' terminus of one of the blocked oligonucleotides; amplifying the coupled oligonucleotide to form an amplified oligonucleotide substantially free of blocking group; and repeating the coupling and amplifying steps with the amplified oligonucleotide until the polynucleotide is prepared.

The present invention also contemplates a method of preparing a library of polynucleotides comprising simultaneously generating a plurality of different polynucleotides, wherein each of the polynucleotides is prepared by coupling a plurality of oligonucleotides using a ligase, wherein at least one of the oligonucleotides is attached to solid support.

Libraries prepared according to the methods recited above are also contemplated by the present invention.

Further embodiments of the present invention include a method of identifying a polynucleotide with a predetermined property, the method comprising generating a library of polynucleotides according any of the methods recited above, and selecting at least one polynucleotide within the library having the predetermined property.

The present invention further includes a method of identifying a polynucleotide with a predetermined property, the method comprising generating a library of polynucleotides according to any of the methods recited above; selecting at least one polynucleotide within the library having the predetermined property; and repeating the generating and selecting steps wherein at least one oligonucleotide of the selected polynucleotides is preferentially incorporated into the library.

Figure 1:
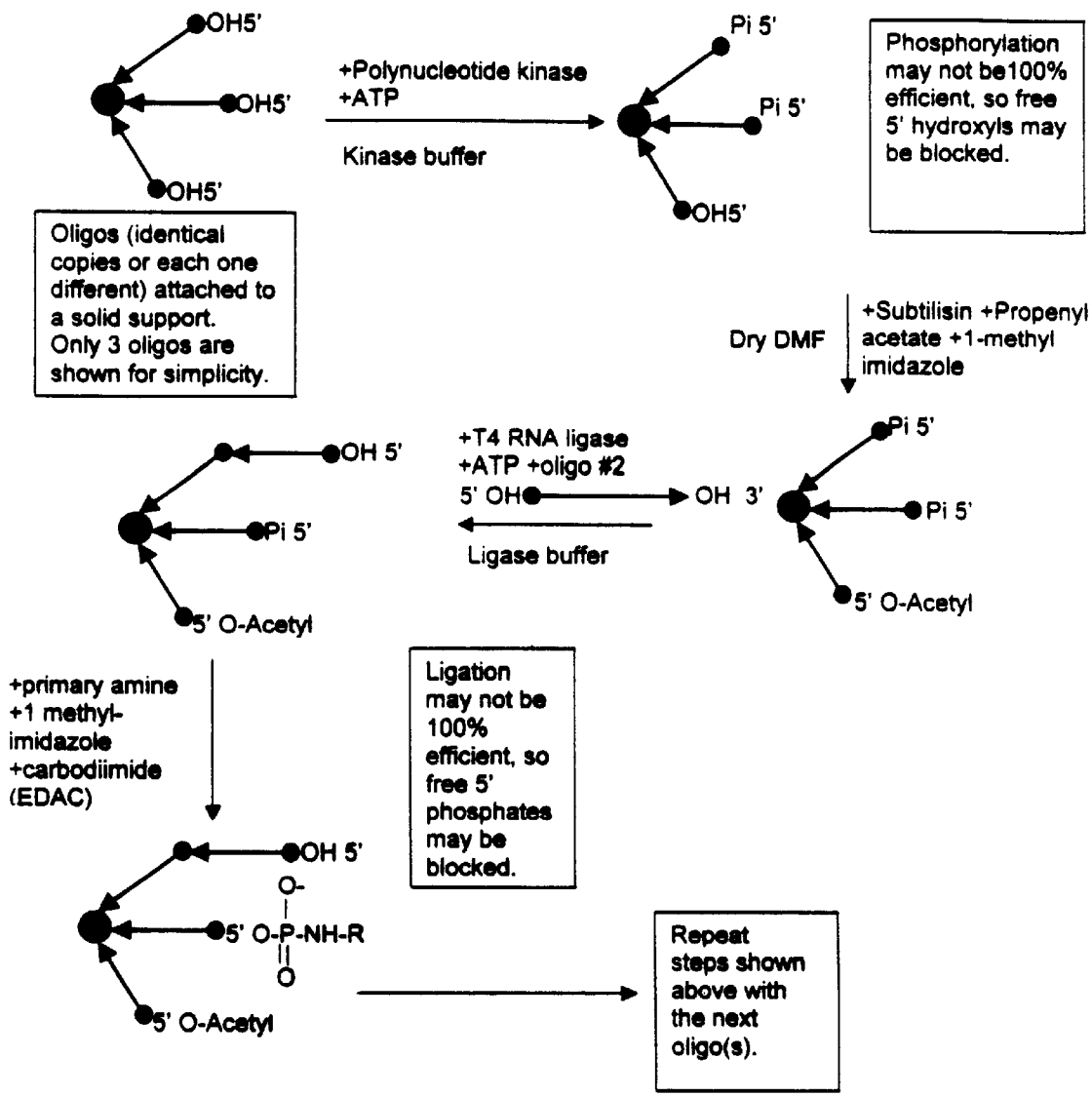
FIG. 1 shows a representative scheme for preparing a polynucleotide in the 3' to 5' direction.

DESCRIPTION OF PREFERRED
EMBODIMENTS OF THE INVENTION

The present invention provides, inter alia, methods of preparing large polynucleotides (such as RNA or DNA molecules longer than 200 bp) of arbitrary or predefined sequence. This process consists of the sequential assembly of oligonucleotides into a large polynucleotide through the use of enzymes (or other catalysts), uncatalyzed chemical reactions, and solid phase synthesis methods.

As used herein, the term "about" means ±5% of the value it modifies.

As used herein, the term "polynucleotide" means a polymer of nucleotides including ribonucleotides and deoxyribonucleotides, and modifications thereof, and combinations thereof. Preferred nucleotides include, but are not limited to, adenine, guanine, cytosine, thymine, and uracil. Modified nucleotides include, but are not limited to, 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentenyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine, 2-O-methyluridine, and the like. The polynucleotides of the invention can also comprise both ribonucleotides and deoxyribonucleotides in the same polynucleotide (e.g. a chimera).

As used herein, the term "oligonucleotide" means a polymer of nucleotides including ribonucleotides and deoxyribonucleotides, and modifications thereof, and combinations thereof, as described above having up to about 200 nucleotides. The polynucleotides of the invention comprise a plurality of oligonucleotides.

As used herein, the phrase "tethered oligonucleotide" means an oligonucleotide that is attached to a solid support or an oligonucleotide attached to a compound that is soluble under certain conditions (facultative solid). An example of such a compound is a plasmid (or any other large DNA molecule) that is soluble in water or buffer but insoluble in a cold (<4° C.) solution of 0.3 M sodium acetate and ~70% ethanol.

As used herein, the term "viroid" means a viral polynucleotide.

As used herein, the term "contacting" means the bringing together of compounds to within distances that allow for intermolecular interactions and/or transformations. At least one "contacting" compound is preferably in the solution phase. Other "contacting" compounds may be attached to solid phase.

"Washing," as used herein, refers to a step in a synthetic process that involves the removal of byproduct, excess reagent, solvent, buffer, any undesirable material, or any combination thereof, from a reaction product. Washing is facilitated when the reaction product is attached to solid phase and the unwanted material is in solution phase.

The term "library," as used herein, refers to a plurality of polynucleotides or polypeptides in which the members have different sequences. "Combinatorial library" indicates a library prepared by combinatorial methods.

As used herein, the term "screening" or "screen" refers to processes for assaying large numbers of library members for a "predetermined property" or desired characteristic. "Predetermined properties" include any distinguishing characteristic, such as structural or functional characteristics, of a polynucleotide or polypeptide including, but not limited to, primary structure, secondary structure, tertiary structure, encoded enzymatic activity, catalytic activity, stability, or ligand binding affinity. Some predetermined properties pertaining to enzyme and catalytic activity include higher or lower activities, broader or more specific activities, and activity with previously unknown or different substrates relative to wild type. Some predetermined properties related to ligand binding include, but are not limited to, weaker or stronger binding affinities, increased or decreased enantioselectivities, and higher or lower binding specificities relative to wild type. Other predetermined properties may be related to the stability of proteins, preferably enzymes, with respect to organic solvent systems, temperature, and sheer forces (i.e., stirring and ultrafiltration). Further, predetermined properties may be related to the ability of a protein to function under certain conditions related to temperature, pH, salinity, and the like. Predetermined properties are often the goal of directed evolution efforts in which a protein or nucleic acid is artificially evolved to exhibit new and/or improved properties relative to wild type.

As used herein, the phrase "ligand binding" refers to a property of a molecule that has binding affinity for a ligand. Ligands are typically small molecules such as, but not limited to, peptides, hormones, and drugs that bind to ligand-binding proteins such as, but not limited to, biological receptors, enzymes, antibodies, and the like.

The present invention is directed to methods of preparing a polynucleotide having at least 200 nucleotides and having a predetermined nucleotide sequence. Preferably, the polynucleotide comprises at least 200 nucleotides. More preferably, the polynucleotide comprises between about 400 nucleotides and about 100,000 nucleotides, more preferably between about 750 nucleotides and about 50,000 nucleotides, and even more preferably between about 1000 nucleotides and 10,000 nucleotides. The polypeptide can be RNA, DNA, or a combination thereof. The polynucleotide is preferably a gene, a portion of a gene, or a plasmid, cosmid, viral genome, bacterial genome, mammalian genome, origins of replication, and the like.

A polynucleotide having a predetermined nucleotide sequence comprising N nucleotides, whose synthesis is desired, is dissected into a plurality of contiguous oligonucleotide fragments of at least two nucleotides and at most N-2 nucleotides. The length of the oligonucleotides can vary as desired, but can be between about 10 nucleotides and about 150 nucleotides, more preferably between about 15 nucleotides and 100 nucleotides, and more preferably between about 25 nucleotides and 75 nucleotides. A convenient oligonucleotide length, for example, may be 100 nucleotides, such that, for example, a 2000 bp polynucleotide will be synthesized by the assembly of 20 contiguous oligonucleotides. Although it is convenient to dissect a polynucleotide into oligonucleotide fragments of equal size, this is not necessary. Each of the oligonucleotides can be prepared using commercially available methods using conventional technology such as, for example, nucleic acid synthesizers. Although purification of the synthesized oligonucleotides may not be necessary, such a step will generally increase the yield of the desired polynucleotide final product. Oligonucleotide suppliers can perform synthesis and purification at reasonable rates.

The set of contiguous oligonucleotide fragments derived from the dissected polynucleotide having nucleotide sequences which, when assembled in order, correspond to the entire nucleotide sequence of the polynucleotide make up the "plurality of oligonucleotides." Preferably, the oligonucleotides within the plurality of oligonucleotides are in solution. It is the combination, or assembly, of the nucleotide sequences of each of the oligonucleotide fragments that comprises the entire nucleotide sequence of the polynucleotide desired to be prepared. In addition, if a degenerate set of polynucleotides encoding a particular protein is desired to be prepared, a set of degenerate oligonucleotides can be prepared accordingly. Thus, for example, a set of 3'-most oligonucleotides can be prepared where, for example, the third position within a codon varies. Such a set can be prepared for each oligonucleotide within the polynucleotide such that all possible combinations of degenerate polynucleotides are produced.

In some embodiments of the invention, the 5' terminus of one or more of the oligonucleotides within the plurality of oligonucleotides is phosphorylated during or after the synthesis of the oligonucleotide. Thus, one or more of the oligonucleotides within the plurality of oligonucleotides can be phosphorylated prior to contacting the oligonucleotide with the solid support. Phosphorylation can be achieved by methods known to those skilled in the art including, but not limited to, using a phosphoramidite or kinase.

The oligonucleotides can be immobilized on a solid support through any number of well known covalent linkages or non-covalent interactions. A preferred solid support is selected from the group consisting of, but not limited to, agarose, polyacrylamide, magnetic beads, polystyrene, polyacrylate, controlled-pore glass, hydroxyethylmethacrylate, polyamide, polyethylene, polyethyleneoxy, polyethyleneoxy/polystyrene copolymer, and the like. Additional examples of solid support and methods of immobilizing oligonucleotides thereto are described in, for example, U.S. Pat. No. 5,942,609, which is incorporated herein by reference in its entirety.

In one embodiment of the invention, preparation of the polynucleotide can be achieved in the 3' to 5' direction. The solid support is contacted with the 3' terminus of a first oligonucleotide from the plurality of oligonucleotides to form a tethered oligonucleotide. The first oligonucleotide is, thus, the 3' most oligonucleotide fragment of the polynucleotide. The first oligonucleotide is attached to the solid support such that its 5'-OH or 5' phosphate functional group is available to react further in the process. This linkage to a solid support can be achieved in a number of different ways as described in, for example, U.S. Pat. No. 5,942,609. As described above, the 5' terminus of this oligonucleotide can be phosphorylated prior to contacting the oligonucleotide with the solid phase. Alternately, the 5' terminus of the oligonucleotide can be phosphorylated after contacting the oligonucleotide with the solid phase. In this manner, it is the 5' terminus of the tethered oligonucleotide that is phosphorylated. Such phosphorylation can be carried out, for example, with a phosphoramidite (Horn et al., *Tetrahedron Lett.*, 1986, 27, 4705–4708, which is incorporated herein by reference in its entirety) or through the use of enzymes such as, but not limited to, polynucleotide kinases which require ATP and various salts.

Phosphorylation of the 5' termini of oligonucleotides may not always be 100% efficient. Whether phosphorylated oligonucleotides are immobilized to the solid support or whether unphosphorylated oligonucleotides are immobilized to the solid support and subsequently phosphorylated, some of the tethered oligonucleotides may not comprise a phosphorylated 5' terminus. Thus, contaminating oligonucleotide assembly products may be produced. In order to minimize the contamination, an optional step in the process can be performed in which the 5' termini are chemically modified in such a way as to prevent their reaction in further steps of the polynucleotide assembly process. Thus, in some embodiments of the invention, prior to ligation of the tethered oligonucleotide to another oligonucleotide within the plurality of oligonucleotides, the tethered oligonucleotide having an unphosphorylated 5' terminus can be capped. Such an optional capping step has no impact on a tethered oligonucleotide which has a phosphorylated 5' terminus. The 5'-OH can be prevented from undergoing inappropriate phosphorylation by a variety of means. Such means include, but are not limited to, use of enzymes which oxidize 5' hydroxyls (e.g., nucleoside oxidase, E.C.1.1.3.28; Isono et al., *Agric. Biol. Chem.,* 1989, 53, 1663–1669, which is incorporated herein by reference in its entirety). Alternately, capping can be carried out with an enzyme that acylates the 5'-OH terminus of the unphosphorylated tethered oligonucleotide. A preferred enzyme is, but is not limited to, a lipase (Uemura et al, *Tetrahedron Lett.,* 1989, 30, 3817–3818, which is incorporated herein by reference in its entirety) or subtilisin (Wong et al., *J. Am. Chem. Soc.,* 1990, 112, 945–953, which is incorporated herein by reference in its entirety), or the like. In addition, particular chemicals known to those skilled in the art can also achieve the desired modification. The capping step may not be necessary to produce useful amounts of the desired full-length polynucleotide.

Once the tethered oligonucleotide is formed, the 3' terminus of another oligonucleotide within the plurality of oligonucleotides, the penultimate 3' oligonucleotide fragment within the polynucleotide, is ligated to the phosphorylated 5' terminus of the tethered oligonucleotide. Ligation can be carried out by co-incubating a ligase, the tethered oligonucleotide, and another oligonucleotide to be ligated to the tethered oligonucleotide. ATP as well as other buffer components are also added (Tessier et al, *Anal. Biochem.,* 1986, 158, 171–178, which is incorporated herein by reference in its entirety; and International Publication WO83/02626, which is incorporated herein by reference in its entirety), as is usually necessary for ligases. The ligation can be carried out with any ligase known to those skilled in the art. Preferably, the ligase is, but is not limited to, an RNA ligase or a ribozyme. More preferably, the RNA ligase is T4 RNA ligase or modified T4 RNA ligase. T4 RNA ligase has been shown to catalyze the ligation of oligonucleotides (Tessier et al., supra, and Shizuya, supra), however, other catalysts can be used. For example, genetically modified versions of T4 RNA ligase with enhanced catalytic activity can be engineered using, for example, methods of directed evolution. The process of directed evolution or in vitro evolution (ive) has been described in detail (Joo et al., *Chem. Biol.,* 1999, 6, 699–706; Joo et al., *Nature,* 1999, 399, 670–673; Miyazaki et al., *J. Mol. Evol.,* 1999, 49, 716–720; Chen et al., *Proc. Natl. Acad. Sci. USA,* 1993, 90, 5618–5622; Chen et al., *Biotechnology,* 1991, 9, 1073–1077; You et al., *Protein Eng,* 1996, 9, 77–83; each of which is incorporated herein by reference in its entirety). In general, the method involves the steps of 1) creating a population of mutant genes; 2) screening this population for individual genes which have a desired property such as coding for an enzyme with improved activity; 3) introducing mutations in the improved gene to create a new population of mutants, and 4) repeating steps 2 and 3 until a desired improvement is achieved. Many methods to introduce mutations exist and are described in the literature (Leung et al., *Technique,* 1989, 1, 11–15; Delagrave et al., *Protein Eng.,* 1993, 6, 327–331; each of which is incorporated herein by reference in its entirety). Similarly, there are many ways to screen mutants for a desired property (Joo et al., *Chem. Biol.,* 1999, 6, 699–706; Joo et al., *Nature,* 1999, 399, 670–673; Miyazaki et al., *J. Mol. Evol.,* 1999, 49, 716–720; Chen et al., *Proc. Natl. Acad. Sci. USA,* 1993, 90, 5618–5622; Chen et al., *Biotechnology,* 1991, 9, 1073–1077; You et al., *Protein Eng,* 1996, 9, 77–83; Marrs et al., *Curr. Opin. Microbiol.,* 1999, 2, 241–245; and U.S. Pat. No. 5,914,245). Improvements in the properties of enzymes (e.g., half-life in organic solvents) achieved using the methods described in the references listed above are frequently one order of magnitude (ten-fold) or greater. Alternatively, ribozymes may be used to ligate oligonucleotides efficiently. Modification of T4 RNA ligase is described below in Example 5. In some embodiments of the invention, the 5' terminus of another oligonucleotide within the plurality of oligonucleotides (e.g., the penultimate 3' oligonucleotide fragment) is phosphorylated prior to ligation to the tethered oligonucleotide. In other embodiments of the invention, the 5' terminus of another oligonucleotide of the plurality of oligonucleotides (e.g., the penultimate 3' oligonucleotide fragment) is not phosphorylated prior to ligation with the tethered oligonucleotide.

Ligation reactions may not be 100% efficient. As a result, contaminating oligonucleotide assembly products missing one or more oligonucleotides can be produced. To avoid excessive accumulation of such assembly products, another optional step can be performed in which the 5' phosphate groups of unligated polynucleotides attached to the solid support are chemically modified in such a way as to prevent their reaction in further steps of the polynucleotide assembly process. The 5' phosphate can be prevented from undergoing further ligation reactions by a variety of means. In some embodiments of the invention, after ligation of the phosphorylated tethered oligonucleotide to another oligonucleotide within the plurality of oligonucleotides, the phosphorylated 5' terminus of any unligated tethered oligonucleotide can be capped. Capping can be carried out by, but not limited to, forming a phosphamide or reaction with a blocking oligonucleotide or the like. Preferably, the blocking oligonucleotide is, but is not limited to, a 5'deoxyoligonucleotide or an oligonucleotide comprising a 5' fluorescent label or other similar blocking agent. Such fluorescent labels are well known to those skilled in the art. A preferred method to block unligated polynucleotides is to form a phosphamide (Chu et al., *Nuc. Acids Res.,* 1988, 16, 3671–3691, which is incorporated herein by reference in its entirety). This is achieved by mixing a solution containing a primary amine, a carbodiimide and, for example, 1-methyl-imidazole with the oligonucleotides attached to the solid support. This capping step may not be necessary to produce useful amounts of the desired full-length polynucleotide. In this manner, those tethered oligonucleotides which failed to undergo a successful ligation with another oligonucleotide within the plurality of oligonucleotides will have a 5' capped terminus that is incapable of allowing the 5' tethered oligonucleotide to be successfully ligated to any other oligonucleotide within the plurality of oligonucleotides.

The ligation steps are repeated with successive contiguous oligonucleotides within the plurality of oligonucleotides until the polynucleotide is prepared. The steps of phosphorylation, capping of unphosphorylated tethered oligonucleotide, and capping of unligated tethered oligonucleotide outlined above can also be repeated, if necessary, to assemble the tethered polynucleotide of the desired length and sequence. Thus, the 5'-most oligonucleotide will be the last oligonucleotide within the plurality of oligonucleotides to be ligated to the ever-elongating tethered oligonucleotide. In some embodiments of the invention, a plurality of different oligonucleotides are contacted with the solid phase simultaneously in order to prepare a plurality of polynucleotides. Between each of the above steps, washes may be necessary to eliminate unreacted compounds and other non-covalently bound contaminants. Also, denaturation steps (e.g., using heat or chemicals such as sodium hydroxide, urea, formamide, etc.) can be added to eliminate oligonucleotides bound non-specifically to the growing polynucleotide chain. Preparation of polynucleotides of the invention in a 3' to 5' direction is summarized in FIG. 1.

In another embodiment of the invention, preparation of the polynucleotide can be achieved in the 5' to 3' direction. The solid support is contacted with the 5' terminus of a first oligonucleotide from the plurality of oligonucleotides to form a tethered oligonucleotide. The first oligonucleotide is, thus, the 5' most oligonucleotide fragment of the polynucleotide. The first oligonucleotide is attached to the solid support such that its 3'-OH group is available to react further in the process with the 5' phosphate group of another oligonucleotide. This linkage to a solid support can be achieved in a number of different ways as described in, for example, U.S. Pat. No. 5,942,609.

The 5' terminus of the remaining oligonucleotides within the plurality of oligonucleotides is phosphorylated prior to contacting the oligonucleotide with the tethered oligonucleotide. Such phosphorylation can be carried out, for example, with a phosphoramidite or kinases as described above. In some embodiments of the invention, the 3' terminus of the oligonucleotide within the plurality of oligonucleotides is blocked in order to avoid self-ligation. Such blocking is carried out by, but not limited to, phosphorylation or using enzymes such as, for example, subtilisin or lipases, which acylate the 3'OH terminus of the oligonucleotide, as described above for 3' to 5' synthesis. This 3' phosphorylation can conveniently be performed by phosphoramidite chemistry as part of the synthesis of the oligonucleotide. Use of these enzymes, however, would preclude the use of acylation as a means of capping unligated oligonucleotides described below. 3' acylation can be performed during the synthesis of the oligonucleotide.

Once the tethered oligonucleotide is formed, the 5' terminus of another oligonucleotide within the plurality of oligonucleotides, the second 5' oligonucleotide fragment within the polynucleotide, is ligated to the 3' terminus of the tethered oligonucleotide. Ligation of the 5' terminus of an oligonucleotide from within the plurality of oligonucleotides to the 3' terminus of the tethered oligonucleotide can be carried out using ligases or ribozymes, as described above. For example, ligation can be achieved by co-incubating a ligase, the tethered oligonucleotide, and the oligonucleotide to be ligated to it. ATP as well as other buffer components are also added, as is usually necessary for ligases. Any of the ligases described above can be used.

As described above for the 3' to 5' synthesis, this ligation reaction may not be 100% efficient. As a result, contaminating oligonucleotide assembly products missing one or more oligonucleotides can be produced. To avoid excessive accumulation of failed sequences, a capping step can be performed wherein the 3'-OH groups of unligated polynucleotides attached to the solid support are chemically modified in such a way as to prevent their reaction in further steps of the polynucleotide assembly process. In some embodiments of the invention, after ligation of another oligonucleotide within the plurality of oligonucleotides, wherein the oligonucleotide comprises a blocked 3' terminus, as described above, to the tethered oligonucleotide, the 3' terminus of any unligated tethered oligonucleotide is capped. In this manner, only unligated tethered oligonucleotides will be capped; ligated tethered oligonucleotides will have a 3' blocking group which is unable to be capped. Capping can be carried out with, for example, an enzyme that acylates the 3'-OH terminus of the unligated tethered oligonucleotide including, but not limited to, a lipase or subtilisin. Alternately, capping can be carried out with an enzyme that adds at least one dideoxy nucleotide to the 3' terminus of the unligated tethered oligonucleotide including, but not limited to, terminal transferase (or any other enzyme with a similar activity). The capping step may not be necessary to produce useful amounts of the desired full-length polynucleotide.

In order for the tethered oligonucleotide to undergo a second ligation to another oligonucleotide within the plurality of oligonucleotides, the 3' blocking moiety must be removed. Thus, in some embodiments of the invention, after ligation of the tethered oligonucleotide to another oligonucleotide having a blocked 3' terminus, the blocked 3' terminus is deblocked. Deblocking can be carried out, for example, by using any adequate phosphatase such as alkaline phosphatase, in the case of a phosphate group, or an enzyme such as, but not limited to, phosphatase, subtilisin, lipase, or the like, in aqueous solvent in the case where the oligonucleotide is blocked by 3' acylation.

Figure 2:
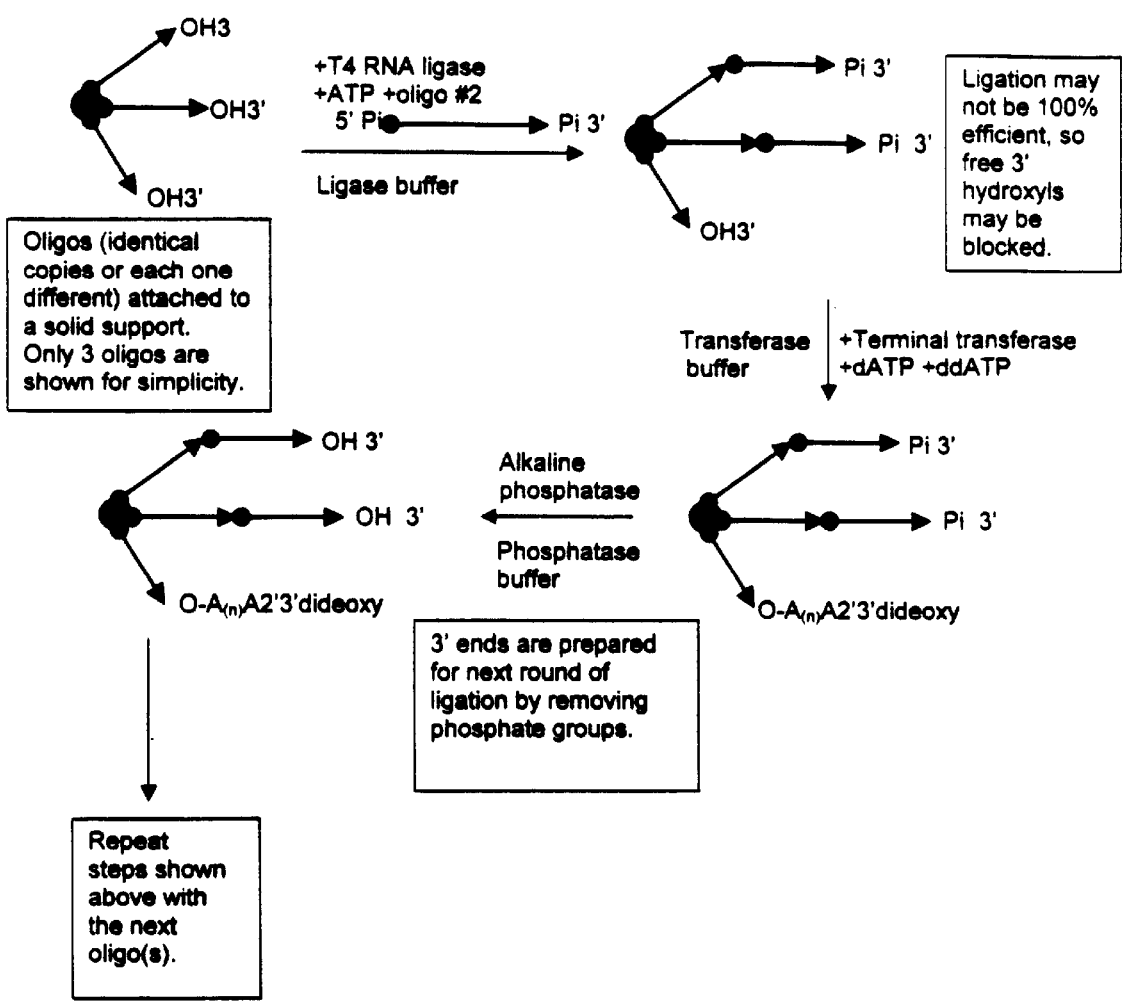
FIG. 2 shows a representative scheme for preparing a polynucleotide in the 5' to 3' direction.

The ligation steps are repeated with successive contiguous oligonucleotides within the plurality of oligonucleotides until the polynucleotide is prepared. The steps of ligation, capping of unligated tethered oligonucleotide, and deblocking outlined above can also be repeated, if necessary, to assemble the tethered polynucleotide of the desired length and sequence. Thus, the 3'-most oligonucleotide will be the last oligonucleotide within the plurality of oligonucleotides to be ligated to the ever-elongating tethered oligonucleotide. In some embodiments of the invention, a plurality of different oligonucleotides are contacted with the solid phase simultaneously in order to prepare a plurality of polynucleotides. Between each of the above steps, washes may be necessary to eliminate unreacted compounds and other non-covalently bound contaminants. Also, denaturation steps (e.g., using heat or chemicals such as sodium hydroxide, urea, formamide, etc.) can be added to eliminate oligonucleotides bound non-specifically to the growing polynucleotide chain. Preparation of polynucleotides of the invention in a 5' to 3' direction is summarized in FIG. 2.

Figure 3:
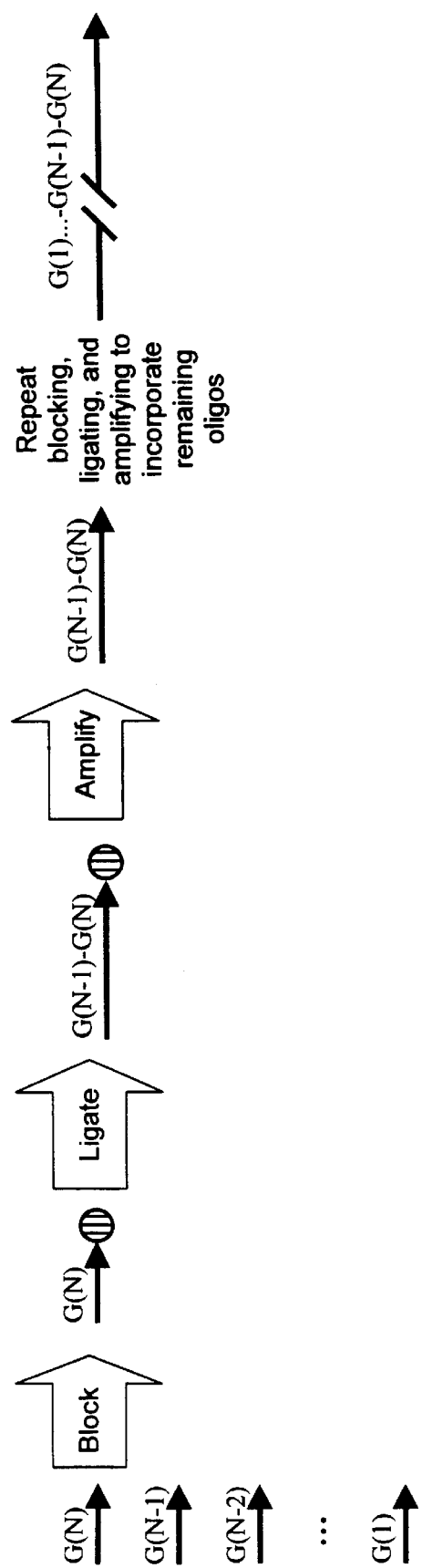
FIG. 3 shows a representative scheme for preparing a polynucleotide in the 3' to 5' direction including an amplification step.

In further embodiments of the present invention an amplification step is incorporated into each cycle after ligation to help overcome possible inefficiencies during oligonucleotide coupling. According to these embodiments, synthesis of a polynucleotide in the 3' to 5' direction may proceed as follows. The 3' terminus of a first oligonucleotide from the plurality of oligonucleotides is blocked with a blocking group to form a blocked oligonucleotide. This first oligonucleotide also comprises the 3' terminus of the polynucleotide to be synthesized. The 5' terminus of the resulting blocked oligonucleotide is coupled to the 3' terminus of a further oligonucleotide from the plurality of oligonucleotides to form a coupled oligonucleotide. The further oligonucleotide preferably represents a portion of the polynucleotide sequence immediately 5' to the first oligonucleotide, and the resulting coupled oligonucleotide retains the blocking group on the 3' end. The coupled oligonucleotide is then amplified, preferably by PCR methods, with concomitant removal of the blocking group. In this way, a relatively inefficient ligation reaction may be employed for each coupling step, obviating the need for capping of failed sequences. The amplification product (amplified oligonucleotide) is then re-blocked at the 3' terminus and subject to the addition of a further oligonucleotide from the plurality of oligonucleotides, repeating the blocking, coupling, and amplifying steps as described above until the full length polynucleotide is formed. This embodiment is summarized in FIG. 3 where oligonucleotides are represented by arrows and arrowheads indicate the 3' ends.

Figure 4:
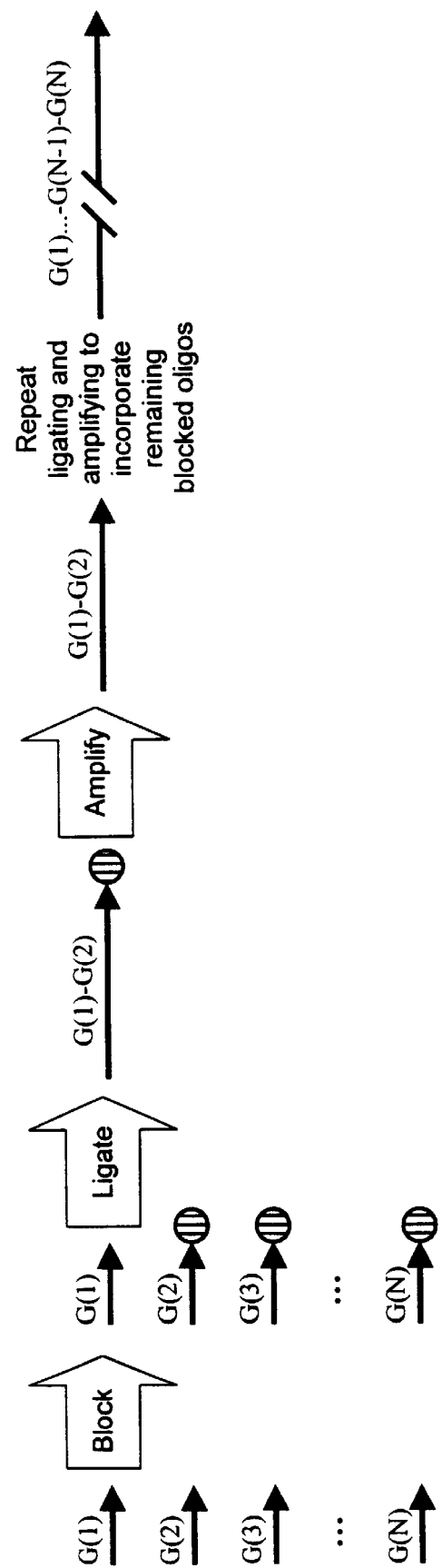
FIG. 4 shows a representative scheme for preparing a polynucleotide in the 5' to 3' direction including an amplification step.

Similarly, methods for the synthesis of polynucleotides incorporating an amplification after each coupling step can be carried out in the 5' to 3' direction. Accordingly, the oligonucleotides comprising the polynucleotide to be synthesized are each blocked with a blocking group at their 3' terminus, with the exception of the oligonucleotide comprising the 5' terminus of the polynucleotide which remains unblocked. The 3' terminus of the unblocked oligonucleotide is coupled to the 5' terminus of one of the blocked oligonucleotides. The blocked oligonucleotide undergoing coupling preferably comprises a region of sequence of the polynucleotide immediately 3' to the sequence of the unblocked oligonucleotide. The resulting coupled oligonucleotide is then amplified, preferably by PCR, with concomitant removal of the blocking group. The amplified product (amplified oligonucleotide) can be coupled with a further blocked oligonucleotide (preferably comprising a region of sequence of the polynucleotide immediately 3' to the sequence of the amplified oligonucleotide) in the same manner as the initial coupling step. Each coupling and amplifying step can be repeated with the generated amplification product and a further blocked oligonucleotide until the full length polynucleotide is generated. This embodiment is summarized in FIG. 4 where oligonucleotides are represented by arrows and arrowheads indicate the 3' ends.

Blocking groups are well known to those skilled in the art and may include 3' enzymatic acylation, a 3' Pi group, and the like. Other suitable blocking groups and methods for their attachment and removal are described in Krug, et al., *Biochemistry* 1982, 21, 1858, which is incorporated herein by reference in its entirety. Preferred blocking groups are capable of attaching to solid support or comprise solid support. A particularly preferred blocking group is ddUTP-biotin, and an even more preferred blocking group is ddUTP-biotin attached to solid support. This blocking group, which can be attached to the 3' end of an oligonucleotide with deoxynucleotidyl transferase, substantially precludes ligation reactions at its site and allows binding of oligonucleotides to solid support. Blocking groups may be cleaved from oligonucleotides by reactions well known to those skilled in the art.

According to the methods of the present invention, the coupling of oligonucleotides is preferably carried out in the presence of a ligase. Ligases are well known to those skilled in the art as enzymes that are capable of ligating the blunt ends of nucleic acids. While not wishing to be bound by theory, it is believed that ligases catalyze the formation of a phosphodiester bond between the 3'-OH group at the end of one nucleic acid and the 5'-phosphate group at the end of another nucleic acid. The mechanism is believed to proceed through a nucleic acid-adenylate intermediate in which an AMP group is attached to the phosphate group at the 5' terminus of a nucleic acid. The activated phosphate group then undergoes nucleophilic attack by the 3'-OH of a further nucleic acid, yielding the coupled nucleic acid. DNA ligases are specific for double-stranded nucleic acids, and their use as ligating reagents is well known to those skilled in the art. In contrast with DNA ligases, RNA ligases are capable of ligating single-stranded nucleic acids.

In view of the proposed ligation mechanism, the coupling of oligonucleotides according to the present invention may comprise several steps. A first step involves contacting a first oligonucleotide to be ligated with a ligase and cosubstrate to form an intermediate activated oligonucleotide. For oligonucleotides that are single-stranded, a preferred ligase is an RNA ligase, such as T4 RNA ligase. Cosubstrates can include ATP, NAD+, or other molecules depending on the specificity of the ligase. For instance, ATP cosubstrate is preferably used with T4 RNA ligase. In some embodiments, the first oligonucleotide is attached to a blocking group, preferably at the 3' end. Alternatively, the blocking group comprises solid support or is attached to solid support to facilitate subsequent manipulations. The activated oligonucleotide is then washed to isolate it from residual reagents or byproducts. Not wishing to be bound by theory, it is thought that the activated oligonucleotide corresponds to an adenylated intermediate (when cosubstrate is ATP) which may be susceptible to nucleophilic attack by AMP byproducts. This side reaction may result in insertions of A or poly-A as well as contribute to poor yields of the desired coupled oligonucleotide. Thus, washing preferably results minimally in the removal of AMP and/or excess ATP from the activated oligonucleotide. The washed oligonucleotide is then contacted with a further oligonucleotide and ligase to form the desired coupled oligonucleotide. Preferably, the further oligonucleotide comprises a free 3'-OH group. The contacting of washed oligonucleotide is preferably performed in the absence of any competing ligase substrates or cosubstrates including, but not limited to, AMP and ATP or other reactants that may interfere with direct coupling of oligonucleotides. The resulting coupled oligonucleotide may be purified by subsequent washing.

Amplification after each coupling step is preferably carried out by PCR. Suitable primers for PCR amplification include oligonucleotides of about 15 to about 30 nucleotides in length and are readily determined by one skilled in the art. Reverse primers include oligonucleotides substantially complementary to the region of sequence comprising the 3' terminus of the coupled oligonucleotide to be amplified, and forward primers include oligonucleotides that are substantially identical to the region of sequence comprising the 5' terminus of the coupled oligonucleotide to be amplified. In some embodiments, forward primers may comprise the 5' most oligonucleotide of the coupled oligonucleotide. Amplification products may be purified by methods well known to those skilled in the art such as, for example, gel electrophoresis and gel extraction techniques.

The amplified oligonucleotide may be isolated prior to repeating the coupling step with a further oligonucleotide. To facilitate isolation, asymmetric PCR may be used during the amplification step. This technique is well known to one skilled in the art and results in an excess of one strand of amplified oligonucleotide. Alternatively, the PCR amplification product may be melted prior to isolation of the coupled oligonucleotide via heat treatment or contacting with denaturants such as urea, N,N-dimethylformamide, NaOH, and the like. The excess or melted strands may be isolated by contacting it with a solid phase to which a substantially complementary oligonucleotide (e.g., a reverse primer from the PCR amplification step) has been attached. Hybridization allows byproducts and reagents to be washed away from the solid phase, thereby isolating and purifying the amplification product for use in a further coupling cycle.

Following completion of the synthesis of the polynucleotide, depending on the particular solid support and linker, the polynucleotide can be cleaved from its solid support or blocking group for processing following synthesis. Cleavage may not be necessary, depending on the solid support and linker, for PCR or RT-PCR to be carried out on the tethered polynucleotide. A polynucleotide encoding all genetic elements necessary for it to be inherited in a stable fashion upon division of its host cell can simply be cleaved from its solid support, circularized by ligation if necessary, and transformed into such a host without any need for amplification or purification. For example, a polynucleotide corresponding to the sequence of LITMUS28 (2,823 bp; New England Biolabs, Beverly, Mass.) can be synthesized, circularized by ligation and transformed into the appropriate strain of *E. coli*. The presence of the M13 origin of replication on this phagemid will allow its single-stranded circular form to replicate in its host, and the ampicillin resistance marker will allow for a selection to isolate only those cells which were transformed by a viable copy of the phagemid. All necessary methods to perform these manipulations can be found in Sambrook, et al., (Eds.), *Molecular Cloning: A Laboratory Manual*, Cold Spring Harbor Laboratory Press: Cold Spring Harbor, N.Y. (1989). The desired polynucleotide can be amplified using the polymerase chain reaction (PCR). If the polynucleotide is an RNA molecule, reverse-transcription-PCR (RT-PCR) can be used to amplify the desired product. PCR or RT-PCR products of the expected molecular weight can be purified by gel electrophoresis. The resulting double-stranded DNA can be used in a variety of experiments, but can also be transformed into a eukaryotic or prokaryotic host such as *E. coli* after adequate preparation as would be obvious to anyone skilled in the art.

The methods of the present invention also include the generation of libraries of polynucleotides using, for instance, the methods of synthesizing polynucleotides disclosed hereinabove. A library represents a plurality of polynucleotides typically generated by randomization or combinatorial methods, that may be screened for members having desirable properties. Libraries can comprise a minimum of two unique members but typically, and desirably, contain a much larger number. Larger libraries are more likely to have members with desirable properties, however, current screening methods have difficulty handling very large libraries (i.e., of more than a few thousand unique members). Thus, preferred libraries comprise from about $10^1$ to about $10^{10}$, or more preferably from about $10^2$ to about $10^6$, or even more preferably from about $10^3$ to about $10^5$ unique polynucleotide members.

According to the present invention, libraries are generated by preparing a plurality of different polynucleotides simultaneously, such as, for example, by combinatorial methods, distinctly contrasting with methods involving non-simultaneous or individual preparation of library members. Polynucleotide members of libraries are prepared by the assembly of oligonucleotides, such as represented by the polynucleotide synthesis methods disclosed hereinabove. The oligonucleotides of the polynucleotide members are preferably enzymatically coupled using a ligase, such as a DNA or RNA ligase. Further, the simultaneous assembly of library members is greatly facilitated using solid phase methods wherein at least one of the components undergoing ligation (i.e., oligonucleotide or polynucleotide intermediate) is attached to solid support. In this fashion, unique library members can be simultaneously assembled when at least one ligation step involves coupling of a mixture of different oligonucleotides to the growing polynucleotide intermediate. As an example, a library of unique polynucleotide members can be prepared according to the method illustrated in FIG. 1 when oligo #2 represents a mixture of different oligonucleotides. In this way, at least one oligonucleotide used to generate the polynucleotide members will vary in sequence and contribute to diversity of the library. Any number of ligation steps during polynucleotide synthesis may involve contacting mixtures of oligonucleotides to the growing polynucleotide intermediate. As a further example, libraries can be generated using the methods illustrated in FIGS. 3 and 4, whereby one or more of the oligonucleotides G(1) to G(N) represent a mixture of different oligonucleotides.

In some embodiments, it may be desirable that oligonucleotide mixtures are represented by degenerate oligonucleotides that encode two or more amino acids at the same position in the same sequence (degeneracies). Degenerate oligonucleotides may be simply designed from inspection of target sequences, such as by observing that a basepair in one target sequence differs from the analogous basepair of another target sequence, and the difference directly corresponds to a difference in encoded amino acids at the same (homologous) position in the sequence. For more complex situations, degenerate oligonucleotides can be designed from amino acid sequences. This approach may be facilitated using the computer program CyberDope which is available online at www.kairos-scientific.com/searchable/cyberdope.html and is described in Delagrave, et al., *Protein Eng.*, 1993, supra., Delagrave, et al., *Biotechnology* 1993 supra., and Goldman, et al., supra. According to this program, a set of amino acids, for instance occupying a variable amino acid site in a set of polypeptides, may be entered, (e.g., A and S, or A, S and T). Based on the amino acids entered, the program calculates a set of degenerate codons which can be used to design a degenerate oligonucleotide encoding the entered amino acids. Degenerate oligonucleotides are readily synthesized by known methods.

Once generated, libraries of polynucleotides may be manipulated directly, or may be inserted into appropriate cloning vectors and expressed. Methods for cloning and expression of polynucleotides, as well as libraries of polynucleotides, are well known to those skilled in the art.

Libraries of polynucleotides, or the expression products thereof, may be screened for members having desirable new and/or improved properties. Any screening method that may result in the identification or selection of one or more library members having a predetermined property or desirable characteristic is suitable for the present invention. Methods of screening are well known to those skilled in the art and include, for example, enzyme activity assays, biological assays, or binding assays. Preferred screening methods include phage display and other methods of affinity selection, including those applied directly to polynucleotides. Other preferred methods of screening involve, for example, imaging technology and colorimetric assays. Suitable screening methods are further described in Marrs, et al., *Curr. Opin. Microbiol.*, 1999, 2, 241; Bylina, et al., *ASM News*, 2000, 66, 211; Joyce, G. F., *Gene*, 1989, 82, 83; Robertson, et al., *Nature*, 1990, 344, 467; Chen, et al., *Proc. Natl. Acad. Sci. USA*, 1993, 90, 5618; Chen, et al., *Biotechnology*, 1991, 9, 1073; Joo, et al., *Chem. Biol.*, 1999, 6, 699; Joo, et al., *Nature*, 1999, 399, 670; Miyazaki, et al., *J. Mol. Evol.*, 1999, 49, 716; You, et al., *Prot. Eng.*, 1996, 9, 77; and U.S. Pat. Nos. 5,914,245 and 6,117,679, each of which is incorporated herein by reference in its entirety.

Polynucleotides identified by screening of a library may be readily isolated and characterized. Preferably, characterization includes sequencing of the identified polynucleotides using standard methods known to those skilled in the art.

In preferred embodiments of the present invention, a recursive screening method may be employed for preparing or identifying a polynucleotide with a predetermined property from a library. An example of a recursive screening method is recursive ensemble mutagenesis described in Arkin, et al., *Proc. Natl. Acad. Sci. USA*, 1992, 89, 7811; Delagrave, et al., *Protein Eng.*, 1993, 6, 327; and Delagrave, et al., *Biotechnology*, 1993, 11, 1548, each of which is herein incorporated by reference in its entirety. According to this method, one or more polynucleotides, having a predetermined property, are identified from a first library by a suitable screening method. The identified polynucleotides are characterized and the resulting information used to assemble a further library. For instance, one or more oligonucleotide components of the identified polynucleotides may be preferentially incorporated into a further library which may also be screened for polynucleotides with a desirable property. Generating a library by incorporating the oligonucleotides identified from a previous cycle can be repeated as many times as desired. Preferably, the recursion is terminated upon identification of one or more library members having a predetermined or desirable property that is superior to the desirable property of the identified polynucleotides of previous cycles or that meets a certain threshold or criterion. According to this method, oligonucleotides that do not lead to functional sequences are eliminated from the pool of oligonucleotides used to generate the next library generation. Furthermore, amounts of oligonucleotides used in the preparation of a further library can be weighted according to their frequency of occurrence in the identified polynucleotides.

In addition to the foregoing embodiments, the present invention also contemplates solid phase techniques of preparing a polynucleotide by ligation of contiguous oligonucleotide fragments in the 5' to 3' or the 3' to 5' direction. The method in the 3' to 5' direction proceeds by contacting solid support with the 3' terminus of a first oligonucleotide from a plurality of oligonucleotides to form a tethered oligonucleotide, ligating the 3' terminus of another oligonucleotide from the plurality of oligonucleotides to the 5' terminus of the tethered oligonucleotide, and repeating the ligation with other oligonucleotides until the polynucleotide is prepared. Similarly, the method in the 5' to 3' direction proceeds by contacting solid support with the 5' terminus of a first oligonucleotide from the plurality of oligonucleotides to form a tethered oligonucleotide, ligating the 5' terminus of another oligonucleotide from the plurality of oligonucleotides to the 3' terminus of the tethered oligonucleotide, and repeating the ligation with other oligonucleotides until the polynucleotide is prepared.

Collectively, the methods of the present invention allow for rapid and controlled "directed evolution" of genes and proteins. The present methods facilitate the preparation of biomolecules having desirable properties that are not naturally known or available. Uses for these improved biomolecules are widespread, promising contributions to the areas of chemistry, biotechnology, and medicine. Enzymes having improved catalytic activities and receptors having modified ligand binding affinities, to name a few, are just some of the possible achievements of the present invention.

Some of the preferred embodiments of the invention described above are outlined below and include, but are not limited to, the following embodiments. As those skilled in the art will appreciate, numerous changes and modifications may be made to the preferred embodiments of the invention without departing from the spirit of the invention. It is intended that all such variations fall within the scope of the invention.

The entire disclosure of each publication cited herein is hereby incorporated by reference.

The following Examples are prophetic.

EXAMPLES

Example 1

3' to 5' Assembly of a 1000 bp Polynucleotide with No Capping

During the incubations described below, the reaction vessel is tumbled end-over-end to keep the beads in suspension.

Step 1. Synthesis. Twenty oligonucleotides, each 50 nucleotides in length are synthesized, deprotected and purified by HPLC according to standard methods. Each oligonucleotide is numbered according to its position in the sequence of the polynucleotide to be synthesized, with the 3'-most oligonucleotide being number 1 and the 5'-most being number 20. Using standard phosphoramidite chemistry, a linker containing a primary amine is attached to the 3'-OH of Oligo #1. The linker is attached such that its amine functional group is free to react with the solid support functional groups during the immobilization step (see below). The linker could be cystamine or an analogous compound with a primary amine at each end of an alkyl chain that contains a disulfide, but reducing agents should then be avoided in subsequent steps of this protocol. The necessary oligonucleotides can be purchased from a commercial supplier such as Operon Inc., or Sigma Inc. All oligonucleotide should have free 5'-OH groups.

Step 2. Immobilization. This step is performed essentially according to the manufacturer's instructions (Pierce Chemical co., Rockford Ill.). For example: In a 1.5 ml microcentrifuge tube, 0.1 µmol of Oligo #1, dissolved in 500 µl conjugation buffer containing 0.1M MES (N-morpholinoethane sulfonic acid) pH 4.7, 0.9% NaCl, is added to 10 mg of Magnabind carboxyl-derivatized magnetic beads prewashed with 1×PBS containing 100 mM phosphate (pH 7.2) and 150 mM NaCl. Fifty µl of 10 mg/ml EDC (1-ethyl-3-(3-dimethylaminopropyl)carbodiimide) is added to the mixture and incubated for 30 minutes at room temperature (20–25° C.). Unreacted COOH groups on the beads can be quenched with a primary amine such as ethylamine or ethanolamine. The amount of Oligo #1 added to the beads can be varied in order to achieve the coupling of ~0.1 µmol of Oligo #1 to the 10 mg of beads.

Step 3. Wash. Unbound oligonucleotides are washed away by removing the solution present in the tube, adding 1 ml of wash buffer W1 containing 25 mM Tris-HCl, pH 7.5, 125 mM NaCl and 1 g/L Tween-20® (polyoxyethylenesorbitan monolaurate), and removing the wash buffer. This wash is performed twice. A final wash using 1 ml of buffer W2 containing 50 mM Tris-Cl pH 8.2, 10 mM $MgCl_2$, 0.1 mM EDTA, 5 mM dithiothreitol, 0.1 mM spermidine is performed. The Magnabeads are conveniently precipitated to the bottom of the microcentrifuge tube by using a magnetic field according to the manufacturer's instructions.

Step 4. Phosphorylation. Oligo #1 (now attached to the solid support) is phosphorylated at its 5'-OH group by adding to the tube 500 µl of buffer P (containing: 50 mM Tris-Cl pH 8.2, 10 mM $MgCl_2$, 0.1 mM EDTA, 5 mM dithiothreitol, 0.1 mM spermidine, 0.4 mM ATP and 200 units of polynucleotide kinase from Roche Molecular Biochemicals) and incubating for 30 minutes at 37° C. (If Oligo #1 was already phosphorylated, this step is not necessary.)

Step 5. Wash. Reagents from the previous step are removed (e.g., by aspiration) and the beads are washed three times with ligation buffer L (minus the ATP and ligase). Finally, the beads are resuspended in 500 µl of buffer L (composition described in step 6) and transferred to a 10 ml conical tube.

Step 6. Ligation. 0.5 µmol of Oligo #2, dissolved in 4.5 ml of buffer L (containing: 50 mM Tris-HCl, pH 8.0, 10 mM $MgCl_2$, 10 tM BSA, 25% polyethylene glycol (PEG 8000), 1 mM hexamine cobalt chloride (HCC), 20 µM ATP and 2000 units of T4 RNA ligase (Roche)) is added to the tube containing the beads and incubated for 4 hours at 25° C.

Alternatively, the beads can be resuspended in 1 ml of buffer L containing 0.5 µmol of Oligo #2 and only 400 units of T4 RNA ligase, incubated for 1 hour at 25° C., precipitated to the bottom of the tube and resuspended in a fresh 1 ml aliquot of buffer L containing 0.5 µmol of Oligo #2 and 400 units of T4 RNA ligase. This procedure is performed a total of 5 times.

Another possibility is to resuspend the beads in 1 ml of buffer L containing 2000 units of T4 RNA ligase and 1 mM ddATP, instead of ATP, and performing a single 4 hour-long incubation at 25° C.

Step 7. Denaturation and wash. The beads are pelleted, and the contents of the tube are removed and 500 µl of wash buffer W1 is added. Without removing wash buffer W1, 500 µl of denaturation buffer containing 0.1 M NaOH and 300 mM NaCl is added into the tube for 1–2 minutes to denature the nascent polynucleotides and fortuitously hybridized oligonucleotides. The beads are then washed twice with 1 ml of wash buffer X containing 0.25 M Tris-HCl, pH 7.5, 0.125 M NaCl, 2 mM $MgCl_2$ and 3 g/l Tween-20®, and once with 1 ml of buffer W2.

Step 8. The nascent polynucleotide is phosphorylated and washed as in steps 4 and 5.

Step 9. The next oligonucleotide (Oligo #n) to be ligated to the nascent polynucleotide is added and incubated as in step 6.

Step 10. Denaturation and wash are performed as in step 7. Steps 8 through 10 are repeated as many times as is necessary to assemble the entire polynucleotide. A total of 19 ligation steps are performed to assemble 20 oligonucleotides.

Step 11. Elution. If the linker used in step 1 was cystamine, 2-mercaptoethanol can be used to elute the polynucleotides from the solid support. A 500 µl volume of solution containing 2-mercaptoethanol 0.1M, dissolved in buffer W1 is added to the beads and incubated for 30 minutes at room temperature. The resulting solution is removed from the beads and transferred to a tube. Ethanol precipitation can be used to partially purify the polynucleotide, and the sample can be stored at −20° C. until needed. Alternatively, a nucleic acid purification kit (Qiaquick purification kit from Qiagen Inc.) can be used to purify and concentrate the polynucleotide.

Step 12. Amplification. An aliquot representing 10 to 50% of the partially purified eluate from step 11 is used as the template of a polymerase chain reaction (PCR). High-fidelity polymerases such as Pfu (Stratagene), Vent (New England Biolabs, Beverly Mass.) or Pwo (www.genaxis.com) can be used in the PCR according to the manufacturers' recommendations. The resulting PCR product is electrophoresed on an agarose gel to allow the isolation of a useful quantity (>10 ng) of a 1 kb double-stranded DNA molecule. This DNA is cloned using methods known to those skilled in the art by using routine methods described in, for example, Sambrook et al. *Molecular Cloning a Laboratory Manual*, Second Ed. Cold Spring Harbor Press (1989) which is incorporated herein by reference in its entirety.) Alternative uses such as in vitro transcription and translation are possible.

Example 2

3' to 5' Assembly of a 1000 bp Polynucleotide with Capping

During the incubations described below, the reaction vessel is tumbled end-over-end to keep the beads in suspension.

Step 1. Synthesis. Twenty oligonucleotides, each 50 nucleotides in length are synthesized, deprotected and purified by HPLC according to standard methods. Each oligonucleotide is numbered according to its position in the sequence of the polynucleotide to be synthesized, with the 3'-most oligonucleotide being number 1 and the 5'-most being number 20. Using standard phosphoramidite chemistry, a linker containing a primary amine is attached to the 3'-OH of Oligo #1. The linker is attached such that its amine functional group is free to react with the solid support functional groups during the immobilization step (see below). The linker could be cystamine or an analogous compound with a primary amine at each end of an alkyl chain that contains a disulfide, but reducing agents should then be avoided in subsequent steps of this protocol. The necessary oligonucleotides can be purchased from a commercial supplier such as Operon Inc., or Sigma Inc. All oligonucleotides should have free 5' OH groups.

Step 2. Immobilization. This step is performed essentially according to the manufacturer's instructions (Pierce Chemical co., Rockford Ill.). For example: In a 1.5 ml microcentrifuge tube, 0.1 µmol of Oligo #1, dissolved in 500 µl conjugation buffer containing 0.1M MES (N-morpholinoethane sulfonic acid) pH 4.7, 0.9% NaCl, is added to 10 mg of Magnabind carboxyl-derivatized magnetic beads prewashed with 1×PBS containing 100 mM phosphate (pH 7.2) and 150 mM NaCl. Fifty µl of 10 mg/ml EDC (1-ethyl-3-(3-dimethylaminopropyl)carbodiimide) is added to the mixture and incubated for 30 minutes at room temperature (20–25° C). Unreacted COOH groups on the beads can be quenched with a primary amine such as ethylamine or ethanolamine. The amount of Oligo #1 added to the beads can be varied in order to achieve the coupling of ~0.1 µmol of Oligo #1 to the 10 mg of beads.

Step 3. Wash. Unbound oligonucleotides are washed away by removing the solution present in the tube, adding 1 ml of wash buffer W1 containing 25 mM Tris-HCl, pH 7.5, 125 mM NaCl and 1 g/L Tween-20®, and removing the wash buffer. This wash is performed twice. A final wash using 1 ml of buffer W2 containing 50 mM Tris-Cl pH 8.2, 10 mM $MgCl_2$, 0.1 mM EDTA, 5 mM dithiothreitol, 0.1 mM spermidine is performed. The Magnabeads are conveniently precipitated to the bottom of the microcentrifuge tube by using a magnetic field according to the manufacturer's instructions.

Step 4. Phosphorylation. Oligo #1 (now attached to the solid support) is phosphorylated at its 5'-OH group by adding to the tube 500 µl of buffer P (containing: 50 mM Tris-Cl pH 8.2, 10 mM MgCl$_2$, 0.1 mM EDTA, 5 mM dithiothreitol, 0.1 mM spermidine, 0.4 mM ATP and 200 units of polynucleotide kinase from Roche Molecular Biochemicals USA) and incubating for 30 minutes at 37° C. (If Oligo #1 was already phosphorylated, this step is not necessary.)

Step 5. Wash. Reagents from the previous step are removed (e.g., by aspiration) and the beads are washed twice with buffer W1 and twice with dry DMF (dimethyl formamide).

Step 6. Capping of non-phosphorylated 5'-OH The beads are resuspended in 1 ml of DMF containing 100 µmol (11 µl) of isopropenyl acetate and 1 mg of subtilisin 8350 and incubated up to 24 hours at 45° C. Subtilisin is a thermostable enzyme described by Pantoliano et al. (*Biochemistry,* 1989, 28, 7205–13, which is incorporated herein by reference in its entirety) that can be constructed as described and prepared according to Wong et al. (*J. Am. Chem. Soc.,* 1990, 112, 945–953) and references listed therein. Thermostable subtilisins (e.g., Esperase) can also be purchased from Novo Nordisk (Denmark).

Step 7. Wash. Reagents from the previous step are removed (e.g., by aspiration) and the beads are washed once with 1 ml of DMF and three times with ligation buffer L (without the ATP and ligase). Finally, the beads are resuspended in 500 µl of buffer L (composition described in step 6) and transferred to a 10 ml conical tube.

Step 8. Ligation. 0.5 µmol of Oligo #2, dissolved in 4.5 ml of buffer L (containing: 50 mM Tris-HCl, pH 8.0, 10 mM MgCl$_2$, 10 µM BSA, 25% polyethylene glycol (PEG 8000), 1 mM hexamine cobalt chloride (HCC), 20 µM ATP and 2000 units of T4 RNA ligase (Roche)) is added to the tube containing the beads and incubated for 4 hours at 25° C.

Alternatively, the beads can be resuspended in 1 ml of buffer L containing 0.5 µmol of Oligo #2 and only 400 units of T4 RNA ligase, incubated for 1 hour at 25° C., precipitated to the bottom of the tube and resuspended in a fresh 1 ml aliquot of buffer L containing 0.5 µmol of Oligo #2 and 400 units of T4 RNA ligase. This procedure is performed a total of 5 times.

Another possibility is to resuspend the beads in 1 ml of buffer L containing 2000 units of T4 RNA ligase and 1 mM ddATP, instead of ATP, and performing a single 4 hour-long incubation at 25° C.

Step 9. Denaturation and wash. The beads are pelleted, the contents of the tube are removed and 500 µl of wash buffer W1 is added. Without removing wash buffer W1, 500 µl of denaturation buffer containing 0.1 M NaOH and 300 mM NaCl is added into the tube for 1–2 minutes to denature the nascent polynucleotides and fortuitously hybridized oligonucleotides. The beads are then washed three times with 1 ml of 1×PBS.

Step 10. Capping of 5' phosphate. An aqueous solution of 0.1M methyl-imidazole pH 7, 0.15M EDC, 0.5M cystamine or another primary amine such as ethylamine or 1-propylamine is added to the beads and incubated for 2 hours at 50° C.

Step 11. Wash. Beads are washed by removing the solution present in the tube, adding 1 ml of wash buffer W1 containing 25 mM Tris-HCl, pH 7.5, 125 mM NaCl and 1 g/L Tween-20®, and removing the wash buffer. This wash is performed twice. A final wash using 1 ml of buffer W2 containing 50 mM Tris-Cl pH 8.2, 10 mM MgCl$_2$, 0.1 mM EDTA, 5 mM dithiothreitol, 0.1 mM spermidine is performed.

Step 12. The nascent polynucleotide is phosphorylated and washed as in steps 4 and 5.

Step 13. After capping and wash (as in steps 6 and 7), the next oligonucleotide (Oligo #n) to be ligated to the nascent polynucleotide is added and incubated as in step 8.

Step 14. Denaturation and wash are performed as in step 9, followed by capping and wash (as in steps 10 and 11). Steps 12 through 14 are repeated as many times as is necessary to assemble the entire polynucleotide. A total of 19 ligation steps are performed to assemble 20 oligonucleotides.

Step 15. Elution. If the linker used in step 1 was cystamine, 2-mercaptoethanol can be used to elute the polynucleotides from the solid support. A 500 µl volume of solution containing 2-mercaptoethanol 0.1M, dissolved in buffer W1 is added to the beads and incubated for 30 minutes at room temperature. The resulting solution is removed from the beads and transferred to a tube. Ethanol precipitation can be used to partially purify the polynucleotide, and the sample can be stored at −20° C. until needed. Alternatively, a nucleic acid purification kit (Qiaquick purification kit from Qiagen Inc.) can be used to purify and concentrate the polynucleotide.

Step 16. Amplification. An aliquot representing 10 to 50% of the partially purified eluate from step 15 is used as the template for PCR. High-fidelity polymerases such as Pfu (Stratagene), Vent (New England Biolabs, Beverly Mass.) or Pwo (www.genaxis.com) can be used in the PCR according to the manufacturers' recommendations. The resulting PCR product is electrophoresed on an agarose gel to allow the isolation of a useful quantity (>10 ng) of a 1 kb double-stranded DNA molecule. This DNA is cloned using methods known to those skilled in the art by methods described in, for example, Sambrook et al. Alternative uses such as in vitro transcription and translation are possible.

Example 3

5' to 3' Assembly of a 1000 bp Polynucleotide with No Capping

During the incubations described below, the reaction vessel is tumbled end-over-end to keep the beads in suspension.

Step 1. Synthesis. Twenty oligonucleotides, each 50 nucleotides in length are synthesized, deprotected and purified by HPLC according to standard methods. Each oligonucleotide is numbered according to its position in the sequence of the polynucleotide to be synthesized, with the 5'-most oligonucleotide being number 1 and the 3'-most being number 20. Using standard phosphoramidite chemistry, a linker containing a primary amine is attached to the 5'-OH of Oligo #1 (e.g., using TFA Aminolink CE phosphoramidite from Perkin-Elmer, Foster City, Calif.). The linker is attached such that its amine functional group is free to react with the solid support functional groups during the immobilization step (see below). The necessary oligonucleotides can be purchased from a commercial supplier such as Operon Inc., or Sigma Inc. Except for Oligo #1, which should have a primary amine at its 5' end and a free 3' hydroxyl, all oligonucleotides should be synthesized with phosphate groups at their 5' and 3' ends.

Step 2. Immobilization. This step is performed essentially according to the manufacturer's instructions (Pierce Chemical co., Rockford Ill.). For example: in a 1.5 ml microcentrifuge tube, 0.1 µmol of Oligo #1, dissolved in 500 µl conjugation buffer containing 0.1M MES (N-morpholinoethane sulfonic acid) pH 4.7, 0.9% NaCl, is added to 10 mg of Magnabind carboxyl-derivatized magnetic beads prewashed with 1×PBS containing 100 mM phosphate (pH 7.2) and 150 mM NaCl. Fifty μl of 10 mg/ml EDC (1-ethyl-3-(3-dimethylaminopropyl)carbodiimide) is added to the mixture and incubated for 30 minutes at room temperature (20–25° C). Unreacted COOH groups on the beads can be quenched with a primary amine such as ethylamine or ethanolamine. The amount of Oligo #1 added to the beads can be varied in order to achieve the coupling of ~0.1 μmol of Oligo #1 to the 10 mg of beads.

Step 3. Wash. Unbound oligonucleotides are washed away by removing the solution present in the tube, adding 1 ml of wash buffer W1 containing 25 mM Tris-HCl, pH 7.5, 125 mM NaCl and 1 g/L Tween-20®, and removing the wash buffer. This wash is performed twice. A final wash using ligation buffer L (without ATP and ligase; composition described in step 4) is performed. Finally, the beads are resuspended in 500 μl of buffer L and transferred to a 10 ml conical tube. (The Magnabeads can be conveniently precipitated using a magnetic field according to the manufacturer's instructions.)

Step 4. Ligation. 0.5 μmol of Oligo #2, dissolved in 4.5 ml of buffer L (containing: 50 mM Tris-HCl, pH 8.0, 10 mM $MgCl_2$, 10 μM BSA, 25% polyethylene glycol (PEG 8000), 1 mM hexamine cobalt chloride (HCC), 20 μM ATP and 2000 units of T4 RNA ligase (Roche)) is added to the tube containing the beads and incubated for 4 hours at 25° C.

Alternatively, the beads can be resuspended in 1 ml of buffer L containing 0.5 μmol of Oligo #2 and only 400 units of T4 RNA ligase, incubated for 1 hour at 25° C., precipitated to the bottom of the tube and resuspended in a fresh 1 ml aliquot of buffer L containing 0.5 μmol of Oligo #2 and 400 units of T4 RNA ligase. This procedure is performed a total of 5 times.

Another possibility is to resuspend the beads in 1 ml of buffer L containing 2000 units of T4 RNA ligase and 1 mM ddATP, instead of ATP, and performing a single 4 hour-long incubation at 25° C.

Step 5. Denaturation and wash. The beads are pelleted, the contents of the tube are removed and 500 μl of wash buffer W1 is added. Without removing wash buffer W1, 500 μl of denaturation buffer containing 0.1 M NaOH and 300 mM NaCl is added into the tube for 1–2 minutes to denature the nascent polynucleotides and fortuitously hybridized oligonucleotides. The beads are then washed by removing the solution present in the tube, adding 1 ml of wash buffer X containing 0.25 M Tris-HCl, pH 7.5, 0.125 M NaCl, 2 mM $MgCl_2$ and 3 g/l Tween-20®, and removing the wash buffer. This wash is performed twice. A final wash with 1 ml of phosphatase buffer (100 mM NaCl, 50 mM Tris-HCl, 10 mM $MgCl_2$, 1 mM dithiothreitol (pH 7.9 at 25° C.)) is performed.

Step 6. Deprotection. The 3' phosphates of the nascent polynucleotides are removed by adding to the beads 1000 units of calf intestinal phosphatase (New England Biolabs, Beverly, Mass.) diluted in 1 ml of phosphatase buffer containing 100 mM NaCl, 50 mM Tris-HCl, 10 mM $MgCl_2$, 1 mM dithiothreitol (pH 7.9 at 25° C.).

Step 7. Phosphatase inactivation. The beads are washed twice with a solution containing 10 mM Tris pH8 and 5 mM EDTA. Any remaining phosphatase is then inactivated by heating the beads to 75° C. for 10 minutes in 1 ml of 5 mM EDTA (pH 8.0).

Step 8. Steps 3 to 7 are repeated as many times as is necessary to assemble the entire polynucleotide. A total of 19 ligation steps are performed to assemble 20 oligonucleotides.

Step 9. After washing the beads, and the polynucleotide attached to them, three times with water and once with PCR buffer (typically supplied by manufacturers of thermostable polymerases) an aliquot representing 10 to 50% of the magnabeads is added directly to a PCR mixture. High-fidelity polymerases such as Pfu (Stratagene), Vent (New England Biolabs, Beverly Mass.) or Pwo (www.genaxis.com) can be used in the PCR according to the manufacturers' recommendations. The resulting PCR product is electrophoresed on an agarose gel to allow the isolation of a useful quantity (>10 ng) of a 1 kb double-stranded DNA molecule. This DNA is cloned using methods known to those skilled in the art. Alternative uses of the polynucleotide or its amplification product, such as templates for in vitro transcription and in vitro translation, are also possible.

Example 4

5' to 3' Assembly of a 1000 bp Polynucleotide with Capping

During the incubations described below, the reaction vessel is tumbled end-over-end to keep the beads in suspension.

Step 1. Synthesis. Twenty oligonucleotides, each 50 nucleotides in length are synthesized, deprotected and purified by HPLC according to standard methods. Each oligonucleotide is numbered according to its position in the sequence of the polynucleotide to be synthesized, with the 5'-most oligonucleotide being number 1 and the 3'-most being number 20. Using standard phosphoramidite chemistry, a linker containing a primary amine is attached to the 5'-OH of Oligo #1 (e.g., using TFA Aminolink CE phosphoramidite from Perkin-Elmer, Foster City, Calif.). The linker is attached such that its amine functional group is free to react with the solid support functional groups during the immobilization step (see below). The necessary oligonucleotides can be purchased from a commercial supplier such as Operon Inc., or Sigma Inc. Except for Oligo #1, which should have a primary amine at its 5' end and a free 3' hydroxyl, all oligonucleotides should be synthesized with phosphate groups at their 5' and 3' ends.

Step 2. Immobilization. This step is performed essentially according to the manufacturer's instructions (Pierce Chemical co., Rockford Ill.). For example: in a 1.5 ml microcentrifuge tube, 0.1 μmol of Oligo #1, dissolved in 500 μl conjugation buffer containing 0.1M MES (N-morpholinoethane sulfonic acid) pH 4.7, 0.9% NaCl, is added to 10 mg of Magnabind carboxyl-derivatized magnetic beads prewashed with 1×PBS containing 100 mM phosphate (pH 7.2) and 150 mM NaCl. Fifty μl of 10 mg/ml EDC (1-ethyl-3-(3-dimethylaminopropyl)carbodiimide) is added to the mixture and incubated for 30 minutes at room temperature (20–25° C.). Unreacted COOH groups on the beads can be quenched with a primary amine such as ethylamine or ethanolamine. The amount of Oligo #1 added to the beads can be varied in order to achieve the coupling of ~0.1 μmol of Oligo #1 to the 10 mg of beads.

Step 3. Wash. Unbound oligonucleotides are washed away by removing the solution present in the tube, adding 1 ml of wash buffer W1 containing 25 mM Tris-HCl, pH 7.5, 125 mM NaCl and 1 g/L Tween-20®, and removing the wash buffer. This wash is performed twice. A final wash using ligation buffer L (minus the ATP and ligase; composition described in step 4) is performed. Finally, the beads are resuspended in 500 μl of buffer L and transferred to a 10 ml conical tube. (The Magnabeads can be conveniently precipitated using a magnetic field according to the manufacturer's instructions.)

Step 4. Ligation. 0.5 μmol of Oligo #2, dissolved in 4.5 ml of buffer L (containing: 50 mM Tris-HCl, pH 8.0, 10 mM MgCl$_2$, 10 μM BSA, 25% polyethylene glycol (PEG 8000), 1 mM hexamine cobalt chloride (HCC), 20 μM ATP and 2000 units of T4 RNA ligase (Roche)) is added to the tube containing the beads and incubated for 4 hours at 25° C.

Alternatively, the beads can be resuspended in 1 ml of buffer L containing 0.5 μmol of Oligo #2 and only 400 units of T4 RNA ligase, incubated for 1 hour at 25° C., precipitated to the bottom of the tube and resuspended in a fresh 1 ml aliquot of buffer L containing 0.5 μmol of Oligo #2 and 400 units of T4 RNA ligase. This procedure is performed a total of 5 times.

Another possibility is to resuspend the beads in 1 ml of buffer L containing 2000 units of T4 RNA ligase and 1 mM ddATP, instead of ATP, and performing a single 4 hour-long incubation at 25° C.

Step 5. Denaturation and wash. The beads are pelleted, the contents of the tube are removed and 500 μl of wash buffer W1 is added. Without removing wash buffer W1, 500 μl of denaturation buffer containing 0.1 M NaOH and 300 mM NaCl is added into the tube for 1–2 minutes to denature the nascent polynucleotides and fortuitously hybridized oligonucleotides. The beads are then washed twice with 1 ml of 1×PBS, and twice with 1 ml of dry DMF (dimethyl formamide).

Step 6. Capping of non-phosphorylated 3' OH. The beads are resuspended in 1 ml of DMF containing 100 μmol (11 μl) of isopropenyl acetate and 1 mg of subtilisin 8350 and incubated up to 24 hours at 45° C.

Step 7. Wash. Beads are washed twice with DMF, twice with wash buffer W1 containing 25 mM Tris-HCl, pH 7.5, 125 mM NaCl and 1 g/L Tween-20®, and once with phosphatase buffer (100 mM NaCl, 50 mM Tris-HCl, 10 mM MgCl$_2$, 1 mM dithiothreitol, pH 7.9 at 25° C.)].

Step 8. Deprotection. The 3' phosphates of the nascent polynucleotides are removed by adding to the beads 1000 units of calf intestinal phosphatase (New England Biolabs, Beverly, Mass.) diluted in 1 ml of phosphatase buffer containing 100 mM NaCl, 50 mM Tris-HCl, 10 mM MgCl$_2$, 1 mM dithiothreitol (pH 7.9 at 25° C.).

Step 9. Phosphatase inactivation. The beads are washed twice with a solution containing 10 mM Tris pH8 and 5 mM EDTA. Any remaining phosphatase is then inactivated by heating the beads to 75° C. for 10 minutes in 1 ml of 5 mM EDTA (pH 8.0).

Step 10. Steps 3 to 9 are repeated as many times as is necessary to assemble the entire polynucleotide. A total of 19 ligation steps are performed to assemble 20 oligonucleotides.

Step 11. After washing the beads, and the polynucleotide attached to them, three times with water and once with PCR buffer (typically supplied by manufacturers of thermostable polymerases) an aliquot representing 10 to 50% of the magnabeads is added for PCR. High-fidelity polymerases such as Pfu (Stratagene), Vent (New England Biolabs, Beverly Mass.) or Pwo (www.genaxis.com) can be used in the PCR according to the manufacturers' recommendations. The resulting PCR product is electrophoresed on an agarose gel to allow the isolation of a useful quantity (>10 ng) of a 1 kb double-stranded DNA molecule. This DNA is cloned using methods known to those skilled in the art. Alternative uses of the polynucleotide or its amplification product such as templates for in vitro transcription and in vitro translation are also possible.

Example 5

Directed Evolution of T4 RNA Ligase (g63)

First, g63 is subcloned by PCR into a convenient expression vector such as pBADmyc/hisA (Invitrogen, Carlsbad, Calif.) using a publicly available gene as a template (ATCC, Manassas, Va.) and appropriate primers. Specifically, primers sph1 (5' GCGAAGCGGCATGCATAATG; SEQ ID NO:1) and badmcs_xho_ant (5' GTTCTTGCATCTC-GAGATTCCTCCTGTTAGCCCAAAAAACG; SEQ ID NO:2) are used to amplify via PCR a fragment of plasmid pBADmyc/hisA (Invitrogen, Carlsbad, Calif.). Primers T4_xho_sns (5' GGAATCTCGAGATGCAAGAACTTTT-TAACAATTTAATGG; SEQ ID NO:3) and T4_Hind_ant (5' CGAGGGACTTGTAAAGCTTCTAGTATC-CTTCTGGG; SEQ ID NO:4) are used to amplify g63 by PCR. All primers are synthesized by Operon (Alameda, Calif.). The two PCR products are fused into a single DNA fragment via overlap PCR. Briefly, a standard PCR reaction is performed wherein the two PCR products described above are mixed together as templates in roughly equimolar amounts along with two primers (sph1 and T4_Hind_ant). The PCR reaction is allowed to proceed normally to yield a DNA fragment that is then cloned into pBADmyc/hisA by restriction digestion and ligation according to well established methods using SphI and HindIII restriction sites both present in the PCR product and plasmid. The resulting construct is called pBADg63.

A population of mutant g63 genes (mutant library) is then constructed, for example by error-prone PCR. The g63 gene is amplified via error-prone PCR using oligonucleotides which introduce appropriate unique restriction sites at the 5' and 3' ends of the gene (e.g., T4_xho_sns and T4_Hind_ant). The resulting PCR product is a population of mutated g63 genes that can be cloned, using standard methods into plasmid pBADg63 via XhoI and HindIII restriction sites present in both PCR product and plasmid. The library thus obtained is then screened for RNA ligase variants with improved activity.

Since most variants will be similar to or less active than wild-type (wt), a screen that can evaluate thousands of clones in a few days is preferred. This can be achieved, for example, by a robotic system which picks individual bacterial colonies, grows them in 96-well plates containing a growth medium such as LB supplemented with carbenicillin (60 μg/ml) and L-arabinose at a concentration of 0.002% to 0.2% (wt/vol). The cultures are grown at 30 to 37° C. for 12 to 24 hours to express useful amounts of RNA ligase, wt or variant. A lysis agent such as B-PER (Pierce, Ill.) is added by a robot to the grown cultures to release the expressed RNA ligase from the bacterial cells (i.e., lyse the cells). An aliquot of each lysate is transferred robotically from a well of a growth plate to a well of a corresponding 96-well assay plate containing reagents that will allow automated monitoring of the reaction catalyzed by RNA ligase variants.

To evolve an RNA ligase that efficiently ligates oligonucleotides, each mutant must be screened for this activity. The reagents of the assay plate therefore include a donor and an acceptor oligonucleotide (1 μM each), 50 mM Tris-Cl, pH 8.0, 10 mM MgCl$_2$, 10 μM BSA, 25% polyethylene glycol (PEG 8000), 1 mM hexamine cobalt chloride (HCC), 20 μM ATP and a molecular beacon that specifically recognizes the ligation product of the donor and acceptor oligonucleotides. As the RNA ligase variant catalyzes the ligation of the donor and acceptor oligonucleotides, molecular beacon molecules will emit a fluorescence signal that increases with time. Assay plate wells in which fluorescence increases more rapidly than control wells containing wild type RNA ligase indicate the presence of a variant with improved activity.

Example 6

Synthesis of a Polynucleotide in the 5' to 3' Direction Incorporating Amplification after Ligation Step 1: Oligonucleotide synthesis. Synthesize the following oligonucleotides:

```
G1 (100mer):                              (SEQ ID NO:5)
AGAGGATCCCCGGGTACCGGTAGAAAAAATGAGTAAAGGAGAAGAACTTT
TCACTGGAGTTGTCCCAATTCTTGTTGAATTAGATGGTGATGTTAATGGG G2 (60mer, 5' phosphorylated):            (SEQ ID NO:6)
CACAAATTTTCTGTCAGTGGAGAGGGTGAAGGTGATGCAACATACGGAAA
ACTTACCCTT G3 (60mer, 5' phosphorylated):            (SEQ ID NO:7)
AAATTTATTTGCACTACTGGAAAACTACCGGTTCCATGGCCAACACTTGT
CACTACTTTC G4 (100mer, 5' phosphorylated):           (SEQ ID NO:8)
TCTTATGGTGTTCAATGCTTTTCAAGATACCCAGATCATATGAAACGGCA
TGACTTTTTCAAGAGTGCCATGCCCGAAGGTTATGTACAGGAAAGAACTA pcrG1 (20mer):                            (SEQ ID NO:9)
AGAGGATCCCCGGGTACCGG G2-(20mer):                               (SEQ ID NO:10)
AAGGGTAAGTTTTCCGTATG G3-(20mer):                               (SEQ ID NO:11)
GAAAGTAGTGACAAGTGTTG G4-(20mer):                               (SEQ ID NO:12)
TAGTTCTTTCCTGTACATAA
```

Assembled in the correct order, 5' G1-G2-G3-G4 3', the oligonucleotides result in the 320 bp-long polynucleotide that encodes almost the entire 5' half of the green fluorescent protein (GFP) gene. Oligonucleotides G2-, G3-, and G4- are biotinylated at their 5' end.

Step 2: Loading beads with oligonucleotides. The oligonucleotides of step 1 are resuspended in $H_2O$, at a concentration of 25 μM, and G2, G3 and G4 are labelled with ddUTP-biotin using: 4 μL 25 μM oligonucleotide, 4 μL 5×buffer, 4 μL $CoCl_2$, 1 μL 100 μM ddUTP-biotin, and 1 μL terminal transferase (Roche Molecular Biochemicals, Inc.), 6 μL $H_2O$ for a 20 μL total volume. The oligonucleotides are incubated for 15 minutes at 37° C. Three aliquots of 25 μL of Magnabind streptavidin beads (Pierce, Rockford, Ill.) are washed once with 50 μL of 2×B&W buffer (10 mM Tris-HCl pH 7.5, 1 mM EDTA, 2M NaCl) and resuspended in 25 μL 2×B&W. To 25 μL of washed beads is added 20 μL G2-ddUTP-biotin The same is done for G3- and G4-ddUTP-biotin reactions. The mixtures are incubated 30 minutes at 43° C., mixing on occasion. Supernatant is removed and discarded. 20 μM of biotin (5 uL) is added to the beads and incubated at 43° C. for 10 minutes. Beads are washed once with 100 μL 2×B&W buffer and once in 25 μL of 1×T4 RNA ligase reaction buffer. As a result of the above manipulations, the bead are now loaded with desired oligonucleotides (G2, G3 and G4) and ready for adenylylation.

Step 3: Adenylylation. The following reagents are added to each sample of beads: 2 μL 200 μM rATP, 1 μL T4 RNA ligase, 2 μL 10×RNA ligase buffer, and 15 μL $H_2O$ for a final total volume of 20 μL. This adenylylation is allowed to proceed 16 hours at 25° C. An additional aliquot of T4 RNA ligase can be added and the reaction allowed to continue an additional 16 hours.

Step 4: Ligation & amplification: G1+G2. The adenylylated G2-beads are washed once in 50 μL of $H_2O$ and resuspended in: 5 μL of 25 μM G1, 1 μL T4 RNA ligase, 2 μL 10×RNA ligase buffer, 12 μL $H_2O$, for a final volume of 20 μL. This reaction is incubated 4 to 16 hours at 25° C. Beads are washed twice with 50 μL of 2×B&W and resuspended in 20 μL of $H_2O$.

To amplify the G1-G2 ligation product, PCR is performed on washed G1-G2 beads by adding: 2.5 μL of bead suspension, 2 μL of 25 μM of oligonucleotides pcrG1, 2 μL of 25 μM G2-, 5 μL 10×buffer (Thermopol buffer supplied with Vent), 5 μL 2 mM dNTPs (each), 1 μL Vent (2000 U/mL, from New England Biolabs, Inc., Beverly, Mass.), and $H_2O$ to a final total volume of 50 μL. The cycling conditions for the touch-down PCR are: 90s at 95° C. followed by 25 cycles of three successive incubations for 15 sec at 95° C., 20 sec at 53 to 43° C. and 20 sec at 72° C., followed by a 120 sec incubation at 72° C.

Step 5: Isolation of single-stranded G1-G2. A fresh aliquot of beads (20 μL) is washed twice with 50 μL of 2×B&W, removing all liquid from the beads. Add about 100 ng of gel-purified PCR product from the previous step to washed beads. Alternatively, the same amount of PCR product purified using a Qiaquick PCR purification kit (Qiagen, Inc.) may be used. Incubate 30 minutes to 2 hours at 43° C. Remove supernatant & assay it (e.g., by PAGE) to verify that a significant amount of the PCR product has been bound by the beads. Add 8 μL of 0.1N NaOH to beads & incubate 5 minutes at room temperature to denature the bound DNA. Remove supernatant (containing single-stranded DNA) from the beads and add 8 μL 0.1 N HCl on ice, then add 2 μL of 10×TE (100 mM Tris-Cl pH 8, 10 mM EDTA) buffer and 2 μL of $H_2O$.

Step 6: Ligation & amplification: G1-G2+G3. Add to adenylylated and washed G3 beads: 1 to 26 μL (~2 μmol) of singe-stranded G1-G2 isolated in previous step, 1 μL T4 RNA ligase, 3 μL 10×RNA ligase buffer, $H_2O$ to 30 μL total volume. Ligate 4 h to overnight at 25° C. The resulting ligation product is amplified as described above and the single-stranded DNA of G1-G2-G3 is isolated also as described. It is then ligated to adenylylated G4 beads and the desired product G1234 is amplified.

What is claimed is:

1. A method of preparing a polynucleotide from a plurality of oligonucleotides, said method comprising:
   a) blocking the 3' terminus of a first oligonucleotide with a blocking group to form a blocked oligonucleotide, wherein said first oligonucleotide comprises the 3' terminus of said polynucleotide;
   b) coupling the 3' terminus of a further oligonucleotide from said plurality of oligonucleotides to the 5' terminus of said blocked oligonucleotide to form a coupled oligonucleotide; wherein said coupling is carried out in the presence of an RNA ligase or a ribozyme;
   c) phosphorylating the 5' terminus of said further oligonucleotide;
   d) amplifying said coupled oligonucleotide to form an amplified oligonucleotide substantially free of blocking group; and
   e) repeating steps a) to d) with said amplified oligonucleotide until said polynucleotide is prepared.

2. The method of claim 1 further comprising the step of isolating said amplified oligonucleotide prior to said repeating.

3. The method of claim 1 wherein said coupling comprises ligating said oligonucleotides with said RNA ligase.

4. The method of claim 3 wherein said RNA ligase is T4 RNA ligase or modified T4 RNA ligase.

5. The method of claim 3 wherein said coupling comprises the steps of contacting said blocked oligonucleotide with RNA ligase and cosubstrate to form activated oligonucleotide, washing said activated oligonucleotide to form washed oligonucleotide, and contacting said washed oligonucleotide with said further oligonucleotide and RNA ligase.

6. The method of claim 5 wherein said RNA ligase is T4 RNA ligase or modified T4 RNA ligase and said cosubstrate is ATP.

7. The method of claim 1 wherein said blocking group comprises ddUTP-biotin.

8. The method of claim 1 wherein said blocking group comprises solid support.

9. The method of claim 8 wherein said solid support is selected from the group consisting of agarose, polyacrylamide, magnetic beads, polystyrene, polyacrylate, controlled-pore glass, hydroxyethylmethacrylate, polyamide, polyethylene, polyethyleneoxy, and polyethyleneoxy/polystyrene copolymer.

10. The method of claim 1 wherein said amplifying is carried out using asymmetric PCR.

11. A method of preparing a polynucleotide from a plurality of oligonucleotides, said method comprising:
   a) blocking the 3' terminus of each of said oligonucleotides, except for an unblocked oligonucleotide comprising the 5' terminus of said polynucleotide, with a blocking group to form a plurality of blocked oligonucleotides;
   b) phosphorylating the 5' terminus of each of said blocked oligonucleotides;
   c) coupling the 3' terminus of said unblocked oligonucleotide with the 5' terminus of one of said blocked oligonucleotides, wherein said coupling is carried out in the presence of an RNA ligase or a ribozyme;
   d) amplifying said coupled oligonucleotides to form an amplified oligonucleotide substantially free of blocking groups; and
   e) repeating steps c) and d) with said amplified oligonucleotide until said polynucleotide is prepared.

12. The method of claim 11 further comprising the step of isolating said amplified oligonucleotide prior to said repeating.

13. The method of claim 11 wherein said coupling comprises ligating said oligonucleotides with RNA ligase.

14. The method of claim 13 wherein said RNA ligase is T4 RNA ligase or modified T4 RNA ligase.

15. The method of claim 11 wherein said coupling comprises the steps of contacting said blocked oligonucleotide with RNA ligase and cosubstrate to form activated oligonucleotide, washing said activated oligonucleotide to form washed oligonucleotide, and contacting said washed oligonucleotide with said further oligonucleotide and RNA ligase.

16. The method of claim 15 wherein said RNA ligase is T4 RNA ligase or modified T4 RNA ligase and said cosubstrate is ATP.

17. The method of claim 11 wherein said blocking group comprises ddUTP-biotin.

18. The method of claim 11 wherein said blocking group comprises solid support.

19. The method of claim 18 wherein said solid support is selected from the group consisting of agarose, polyacrylamide, magnetic beads, polystyrene, polyacrylate, controlled-pore glass, hydroxyethylmethacrylate, polyamide, polyethylene, polyethyleneoxy, and polyethyleneoxy/polystyrene copolymer.

20. The method of claim 11 wherein said amplifying is carried out using asymmetric PCR.

21. A method of preparing a library of polynucleotides comprising simultaneously generating a plurality of different polynucleotides, wherein each of said polynucleotides is prepared according to the method of claim 1.

22. A method of preparing a library of polynucleotides comprising simultaneously generating a plurality of different polynucleotides, wherein each of said polynucleotides is prepared according to the method of claim 11.

23. A method of identifying a polynucleotide with a predetermined property, said method comprising generating a library of polynucleotides according to the method of claim 21, and selecting at least one polynucleotide within said library having said predetermined property.

24. A method of identifying a polynucleotide with a predetermined property, said method comprising generating a library of polynucleotides according to the method of claim 22, and selecting at least one polynucleotide within said library having said predetermined property.

25. A method of identifying a polynucleotide with a predetermined property, said method comprising:
   a) generating a library of polynucleotides according to the method of claim 21;
   b) selecting at least one polynucleotide within said library having said predetermined property; and
   c) repeating steps a) and b) wherein at least one oligonucleotide of said selected oligonucleotides is incorporated into a further library.

26. A method of identifying a polynucleotide with a predetermined property, said method comprising:
   a) generating a library of polynucleotides according to the method of claim 22;
   b) selecting at least one polynucleotide within said library having said predetermined property; and
   c) repeating steps a) and b) wherein at least one oligonucleotide of said selected oligonucleotides is incorporated into a further library.

* * * * *

UNITED STATES PATENT AND TRADEMARK OFFICE
CERTIFICATE OF CORRECTION

PATENT NO.    : 6,635,453 B2
DATED         : October 21, 2003
INVENTOR(S)   : Delagrave et al.

It is certified that error appears in the above-identified patent and that said Letters Patent is hereby corrected as shown below:

Column 19,
Line 14, please delete "10 tm BSA," and insert therefore -- 10µM BSA --.

Column 27,
Line 56, please delete "(5uL)" and insert therefore -- (50 ul) --

Signed and Sealed this

Thirteenth Day of April, 2004

JON W. DUDAS
*Acting Director of the United States Patent and Trademark Office*

SEQUENCE LISTING

<160> NUMBER OF SEQ ID NOS: 12

<210> SEQ ID NO 1
<211> LENGTH: 20

```
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 1
gcgaagcggc atgcataatg                                               20

<210> SEQ ID NO 2
<211> LENGTH: 41
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 2
gttcttgcat ctcgagattc ctcctgttag cccaaaaaac g                       41

<210> SEQ ID NO 3
<211> LENGTH: 39
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 3
ggaatctcga gatgcaagaa cttttaaca atttaatgg                           39

<210> SEQ ID NO 4
<211> LENGTH: 35
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 4
cgagggactt gtaaagcttc tagtatcctt ctggg                              35

<210> SEQ ID NO 5
<211> LENGTH: 100
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 5
agaggatccc cgggtaccgg tagaaaaaat gagtaaagga gaagaacttt tcactggagt   60 gtcccaatt cttgttgaat tagatggtga tgttaatggg                          100

<210> SEQ ID NO 6
<211> LENGTH: 60
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 6 cacaaattt ctgtcagtgg agagggtgaa ggtgatgcaa catacggaaa acttaccctt    60

<210> SEQ ID NO 7
```

```
<211> LENGTH: 60
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 7
aaatttattt gcactactgg aaaactaccg gttccatggc caacacttgt cactactttc     60

<210> SEQ ID NO 8
<211> LENGTH: 100
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 8
tcttatggtg ttcaatgctt ttcaagatac ccagatcata tgaaacggca tgacttttc     60 aagagtgcca tgcccgaagg ttatgtacag gaaagaacta                         100

<210> SEQ ID NO 9
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 9
agaggatccc cgggtaccgg                                                20

<210> SEQ ID NO 10
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 10
aagggtaagt tttccgtatg                                                20

<210> SEQ ID NO 11
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 11
gaaagtagtg acaagtgttg                                                20

<210> SEQ ID NO 12
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 12
tagttctttc ctgtacataa                                                20
```